(12) United States Patent
Stull et al.

(10) Patent No.: US 6,322,969 B1
(45) Date of Patent: Nov. 27, 2001

(54) METHOD FOR PREPARING PERMUTED, CHIMERIC NUCLEIC ACID LIBRARIES

(75) Inventors: Robert A. Stull, Alameda; Maria Pallavicini, Livermore; Gary Green, San Francisco, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/085,686

(22) Filed: May 27, 1998

(51) Int. Cl.$^7$ .................................................. C12Q 1/68
(52) U.S. Cl. .................... 435/6; 435/4; 435/5; 435/489; 435/DIG. 46; 435/DIG. 1; 530/23.4; 530/23.1
(58) Field of Search ................................... 435/489, 6, 4, 435/5, DIG. 46, DIG. 1; 530/23.4, 23.1

(56) References Cited

PUBLICATIONS

Ostermeier et al., "Combinatorial protein engineering by incremental truncation", *Pro. Nat'l. Acad. Sci*, 96:3562–3567, Mar. 1999.

Ostermeier et al., A combinatorial approach to hybrid enzymes independent of DNA homology, *Nature Biotechnology*, 17:1205–1209, Dec. 1999.

Clark et al., "Ordered Deletions Using Exonuclease III", *Methods in Molecular Biology*, 57:139–285.

Hobson et al., "Construction of Linker–Scanning Mutations by Oligonucleotide Ligation", *Methods in Molecular Biology*, 57: 279–285.

Cunningham et al., "Receptor and Antibody Epitopes in Human Growth Hormone Identified by Homolog–Scanning Mutagenesis", *Science* 243: 1330–1336 (1989).

Cunningham et al., "High Resolution Epitope Mapping of hGH–Receptor Interactions by Alanine–Scanning Mutagenesis", *Science* 244: 1081–1085 (1989).

Gray et al., "Generation of hybrid amylase plasmids", Abstract.

Harlow et al., "Construction of Linker–Scanning Mutations Using PCR", *Methods in Molecular Biology*, 57: 287–295.

Li et al., "Three–step PCR mutagenesis for 'linker scanning'", *Nucleic Acids Research*, 21:(16) 3745–3748 (1993).

Sailen Barik, "Site–Directed Mutagenesis by Double Polymerase Chain Reaction", *Methods in the Molecular Biology*, 15: 277–287.

Haas et al., "TnMax—a versatile mini–transposon for the analysis of cloned genes and shuttle mutagenesis", *Gene*. 130: 23–31 (1995).

Kahrs et al., "An improved TnMax mini–transposon system suitable for sequencing, shuttle mutagenesis and gene fusions", *Gene* 167: 53–57 (1995).

McCafferty et al., "Construction and Screening of Antibody Display Libraries", *Phage Display of Peptides and Proteins*, 79–111.

Kasahara et al., "Tissue–Specific Targeting of Retroviral Vectors Through Ligand–Receptor Interactions", *Science* 266: 1373–1376 (1994).

Han et al., "Ligand–directed retroviral targeting of human breast cancer cells", *Proc. Natl. Acad. Sci* 92: 9747–9751 (1995).

Krasnykh et al., "Characterization of an Adenovirus Vector Containing a Heterologous Peptide Epitope in the HI Loop of the Fiber Knob", *Journal of Virology*, 1844–1852 (1995).

Somia et al., "Generation of targeted retroviral vectors by using single–chain variable fragment: An approach to invivo gene delivery", *Proc. Natl. Acad. Sci*, 92: 7570–7574 (1995).

Deldine et al., A Chimeric Ty3/Moloney Murine Leukemia Virus Integrase Protein Is Active In Vivo, *Journal of Virology*, 4297–4307 (1998).

*Primary Examiner*—T. D. Wessendorf
(74) *Attorney, Agent, or Firm*—Townsend and Townsend and Crew, LLP

(57) ABSTRACT

The present invention relates to permuted, chimeric nucleic acid libraries and methods of preparing such permuted, chimeric nucleic acid libraries.

10 Claims, 8 Drawing Sheets

METHOD FOR PREPARING PERMUTED, CHIMERIC NUCLEIC ACID LIBRARIES

CROSS REFERENCE TO RELATED APPLICATIONS

Not applicable.

FEDERALLY SPONSORED RESEARCH OR DEVELOPMENT

This invention was made with government support under Grant No. P01-DK50267, awarded by the National Institutes of Health. The government has certain rights in this invention.

FIELD OF THE INVENTION

The present invention relates to permuted, chimeric nucleic acid libraries and methods of preparing such permuted, chimeric nucleic acid libraries.

BACKGROUND OF THE INVENTION

Mutagenesis of nucleic acids has been used to identify essential domains and to create nucleic acids or proteins with altered activity. A number of techniques have been used to examine the effect of simple substitution, deletion or insertion in the sequence of a nucleic acid or protein.: making processive deletions of DNA using exonuclease digestions (see, e.g., Clark & Henikoff, "Ordered Deletions Using Exonuclease III," chapter 12, *Methods in Molecular Biology*, volume 57, *In Vitro Mutagenesis Protocols* (Trower, ed., 1996)); constructing linker scanner mutations with oligonucleotides to examine promoter function or to systematically alter amino acids to examine protein function (McKnight & Kingsbury, *Science* 217:316–324 (1982)); constructing linker scanner mutations with PCR (Li & Shapiro, *Nuc. Acids Res.* 21:3745 (1993); Harlow et al., "Construction of Linker-Scanning Mutations Using PCR," chapter 26, *Methods in Molecular Biology*, volume 57, In Vitro Mutagenesis Protocols (Trower, ed., 1996); and Barik, "Site-directed Mutagenesis by Double Polymerase Chain Reaction," chapter 28, *Methods in Molecular Biology*, volume 15, *PCR Protocols* (White, ed., 1993)); alanine scanning mutagenesis (Cunningham & Wells, *Science* 44:1081 (1989)); by transposon insertion (Rass et al., *Gene* 130:23 (1993); Kahrs et al., *Gene* 167:53 (1995) and by recombination (Gray et al., *J. Bacteriol.* 166:635 (1986).

In addition, nucleic acid and protein function have been studied by examining the effect of chimeric molecules, e.g., by inserting mutated or shuffled nucleic acids into a gene. Typically, the mutated or shuffled domain is from the gene that is being studied, or a close homolog. For example, chimeric molecules have been made by homolog scanning (Cunningham et al., *Science* 241:1330 (1989)); and by PCR ("Construction and Screening of Antibody Display Libraries," Chapter 6, *Phage Display of Peptides and Proteins* (1996)). These techniques are used to systematically reassemble a gene encoding a protein with mutated, homologous, or shuffled domains.

Finally, techniques are also known for inserting fixed heterologous sequences into genes at known positions to create rationally designed chimeras. Examples of this latter approach include manipulation of genes such as env, adenovirus fiber protein, and retrovirus integrase to contain a heterologous, rationally designed sequences of fixed length and at specific positions (Kasahara et al., *Science* 266:1373 (1994); Han et al., *PNAS* 92:9747 (1995); Somia et al., *PNAS* 92:7570 (1995); Krasnykh et al., *J. Virol.* 72:1844 (1998); and Dildine et al., *J. Virol.* 72:4287 (1998)).

In order to screen large numbers of sequences and many combinations of genes, there is a need to develop novel and alternative methods of mutagenizing complex nucleic acids.

SUMMARY OF THE INVENTION

The present invention provides novel methods of making chimeric, combinatorial libraries in which a heterologous nucleic acid sequence is inserted at random between various permuted domains of a target nucleic acid. The methods of the present invention allow production of a large array of permuted nucleic acid sequences, and further allow production of numerous different chimeric nucleic acids. These libraries encode proteins with altered function or provide nucleic acids such as promoters with altered function. A further advantage of the system is that the target nucleic acid is permuted over the length of the sequence from about one to about twenty nucleotides, preferably about one to ten nucleic acids, most preferably about one to about five nucleic acids, providing a comprehensive array of chimeric molecules.

In one aspect, the invention provides a method of making a permuted nucleic acid library, the method comprising the steps of: a. providing backbone nucleic acids comprising a selected nucleic acid, wherein the backbone nucleic acids comprise an exonuclease sensitive site A and wherein the backbone nucleic acids further comprise a primer sequence C flanking the selected nucleic acid; b. bilaterally digesting the backbone nucleic acids at the exonuclease sensitive site A with an exonuclease, wherein the exonuclease permutes the selected nucleic acid from about every one to about every ten nucleotides, to create permuted nucleic acids; c. ligating to the permuted nucleic acids adapters comprising a interior primer sequence B; and d. amplifying the permuted nucleic acids using primers complementary to interior primer sequence B and primer sequence C.

In another aspect, the invention provides a method of making a permuted nucleic acid library, the method comprising the steps of: a. providing backbone nucleic acids comprising a selected nucleic acid, wherein the backbone nucleic acids further comprise a primer sequence C flanking the selected nucleic acid; b. digesting the backbone nucleic acids with DNase I and $Mn^{2+}$, wherein the DNase I permutes the selected nucleic acid from about every one to about every ten nucleotides, to create permuted nucleic acids; c. ligating to the permuted nucleic acids adapters comprising a interior primer sequence B; and d. amplifying the permuted nucleic acids using primers complementary to interior primer sequence B and primer sequence C.

In one embodiment, the method further comprises the step of ligating the permuted nucleic acids to a vector, and cells comprising the vectors. In another embodiment, step a comprises backbone nucleic acids that have a plurality of unique exonuclease sensitive sites. In another embodiment, the amplification reaction further incorporates an exterior primer sequence D adjacent to primer sequence C.

In another aspect, the invention provides a method of making a permuted nucleic acid library, the method comprising the steps of: a. providing backbone nucleic acids comprising a selected nucleic acid, wherein the backbone nucleic acids comprise an exonuclease resistant site R that flanks the selected nucleic acid and an exonuclease sensitive site A, and wherein the backbone nucleic acids further comprise a first monomerization restriction site; b. unilaterally digesting the backbone nucleic acids at the exonuclease sensitive site A with an exonuclease, wherein the exonuclease permutes the selected nucleic acid from about every one to about every ten nucleotides, to create permuted nucleic acids; c. ligating an adapter comprising a second monomerization restriction site to the permuted nucleic acids; and d. digesting the permuted nucleic acids at the monomerization restriction sites.

In one embodiment, step d further comprises circularizing the permuted chimeric acids into vectors by ligating the digested monomerization restriction sites. In another embodiment, the adapter further comprises an interior primer sequence B and the permuted nucleic acids further comprise a primer sequence C. In another embodiment, the permuted nucleic acids are amplified using primer complementary to interior primer sequence B and primer sequence C and wherein the amplification reaction incorporates an exterior primer sequence D adjacent to primer sequence C.

In another aspect, the present invention provides a method of making a permuted, chimeric nucleic acid library, the method comprising the steps of:

(i) permuting a selected nucleic acid by: a. providing backbone nucleic acids comprising the selected nucleic acid, wherein the backbone nucleic acids have an exonuclease sensitive site A and wherein the backbone nucleic acids comprise primer sequences C and Y flanking opposite sides of the selected nucleic acid; b. bilaterally digesting the backbone nucleic acids at the exonuclease sensitive site A with an exonuclease, wherein the exonuclease permutes the selected nucleic acid from about every one to about every ten nucleotides, to create permuted nucleic acids;

(ii) creating 5' permuted nucleic acids by: a. ligating to part of the permuted nucleic acids adapters comprising an interior primer sequence B; and b. amplifying the permuted nucleic acids using primers complementary to interior primer sequence B and primer sequence C, wherein the amplification reaction incorporates an exterior primer sequence D adjacent to primer sequence C;

(iii) preparing 3' permuted nucleic acids by: a. ligating to part of the permuted nucleic acids adapters comprising an interior primer sequence X; and b. amplifying the pennuted nucleic acids using primers complementary to interior primer sequence X and primer sequence Y, wherein the amplification reaction incorporates an exterior primer sequence Z adjacent to primer sequence Y;

(iv) preparing nucleic acid inserts with 5' adapters having interior primer site B, and 3' adapters having interior primer site X;

(v) mixing the 5' permuted nucleic acids, the 3' permuted nucleic acids, and the nucleic acid inserts;

(vi) amplifying the mixture using primers complementary to exterior primer sites D and Z to create permuted, chimeric nucleic acids; and (vii) ligating the permuted, chimeric nucleic acids to a vector, thereby creating a permuted, chimeric nucleic acid library.

In one embodiment, the interior or exterior primers are labeled with a ligand, and steps ii(b) and iii(b) further comprise isolating the permuted nucleic acids by affinity purification.

In another aspect, the invention provides a method of making a permuted, chimeric nucleic acid library, the method comprising the steps of:

(i) creating 5' permuted nucleic acids by: a. providing backbone nucleic acids comprising a selected nucleic acid, wherein the backbone nucleic acids have a resistant site R that flanks the selected nucleic acid, wherein the backbone nucleic acids have an exonuclease sensitive site A, and wherein the backbone nucleic acids have a primer sequence C; b. unilaterally digesting the backbone nucleic acids at the exonuclease sensitive site A with an exonuclease, wherein the exonuclease permutes the selected nucleic acid from about every one to about every ten nucleotides, to create permuted nucleic acids; c. ligating to the permuted nucleic acids adapters comprising an interior primer sequence B; and d. amplifying the permuted nucleic acids using primers complementary to interior primer sequence B and primer sequence C, wherein the amplification reaction incorporates an exterior primer sequence D adjacent to primer sequence C;

(ii) creating 3' permuted nucleic acids by: a. providing backbone nucleic acids comprising the selected nucleic acid, wherein the backbone nucleic acids have an exonuclease resistant site R' that flanks the selected nucleic acid, wherein the backbone nucleic acids have exonuclease sensitive site A, and wherein the backbone nucleic acids have a primer sequence Y; b. unilaterally digesting the backbone nucleic acids at the exonuclease sensitive site A with an exonuclease, wherein the exonuclease permutes the selected nucleic acid from about every one to about every ten nucleotides, to create permuted nucleic acids; c. ligating to the permuted nucleic acids adapters comprising an interior primer sequence X; and d. amplifying the permuted nucleic acids using primers complementary to interior primer sequence X and primer sequence Y, wherein the amplification reaction incorporates an exterior primer sequence Z adjacent to primer sequence Y;

(iii) preparing nucleic acid inserts with 5' adapters containing primer site B, and 3' adapters containing primer site X;

(iv) mixing the 5' permuted nucleic acids, the 3' permuted nucleic acids, and the nucleic acid inserts;

(v) amplifying the using primers complementary to exterior primer sites D and Z to create permuted, chimeric nucleic acids; and (vi) ligating the permuted, chimeric nucleic acids to a vector, thereby creating a permuted, chimeric nucleic acid library.

In one embodiment, the interior or exterior primers are labeled with a ligand, and steps i(d) and ii(d) further comprise isolating the permuted nucleic acids by affinity purification.

In one embodiment, the method her comprises the step of ligating the ipermuted nucleic acids to a vector, and cells comprising the vectors.

In another aspect the invention provides a permuted nucleic acid library, wherein the library comprises permuted nucleic acids that are permuted from about one to about ten nucleotides, and wherein the permuted nucleic acids are flanked by two unique primer sequences.

In one embodiment, the permuted nucleic acids are 5' or 3' permuted nucleic acids. Another embodiment provides cells comprising the libraries of the invention.

In another aspect, the invention provides a permuted, chimeric nucleic acid library, wherein the library comprises permuted, chimeric nucleic acids comprising a 5' permuted nucleic acid, a nucleic acid insert, and a 3' permuted nucleic acid, wherein the permuted nucleic acids are permuted from about one to about ten nucleotides, and wherein the permuted, chimeric nucleic acids are flanked by two unique primer sequences.

In one embodiment, the selected or permuted nucleic acid is derived from a virus family selected from the group consisting of a retrovirus, an adenovirus, and an adeno-associated virus. In another embodiment, the adenovirus nucleic acid encodes a fiber protein. In another embodiment, the retrovirus nucleic acid is derived from a retrovirus virus subfamily Oncovinnae, Lentivinnae, or Spumavirinae. In another embodiment, the retrovirus nucleic acid is an env gene, an integrase gene, or an LTR. In another embodiment, the env gene is selected from the group consisting of amphotropic MLV env, ecotropic MLV env, HIV-1 env, HIV-2 env, HTLV-1 env, HTLV-2 env, FIV env, SIV env, BIV env, avian spleen necrosis virus env, and HFV env.

In one embodiment, the nucleic acid insert is selected from the group consisting of growth factors, cytokines, and chemokines. In another embodiment, the nucleic acid insert is a random peptide. In another embodiment, the nucleic acid insert is selected from the group consisting of c-kit, Il-2, Il-3, Il-6, IGF-I, IGF-II, INF-γ, FGF, TGF, TNF-α, TNF-β, NGF, BDNF, CNTF, flt31, and protein A.

DETAILED DESCRIPTION OF THE INVENTION

I. Introduction

Figure 1:
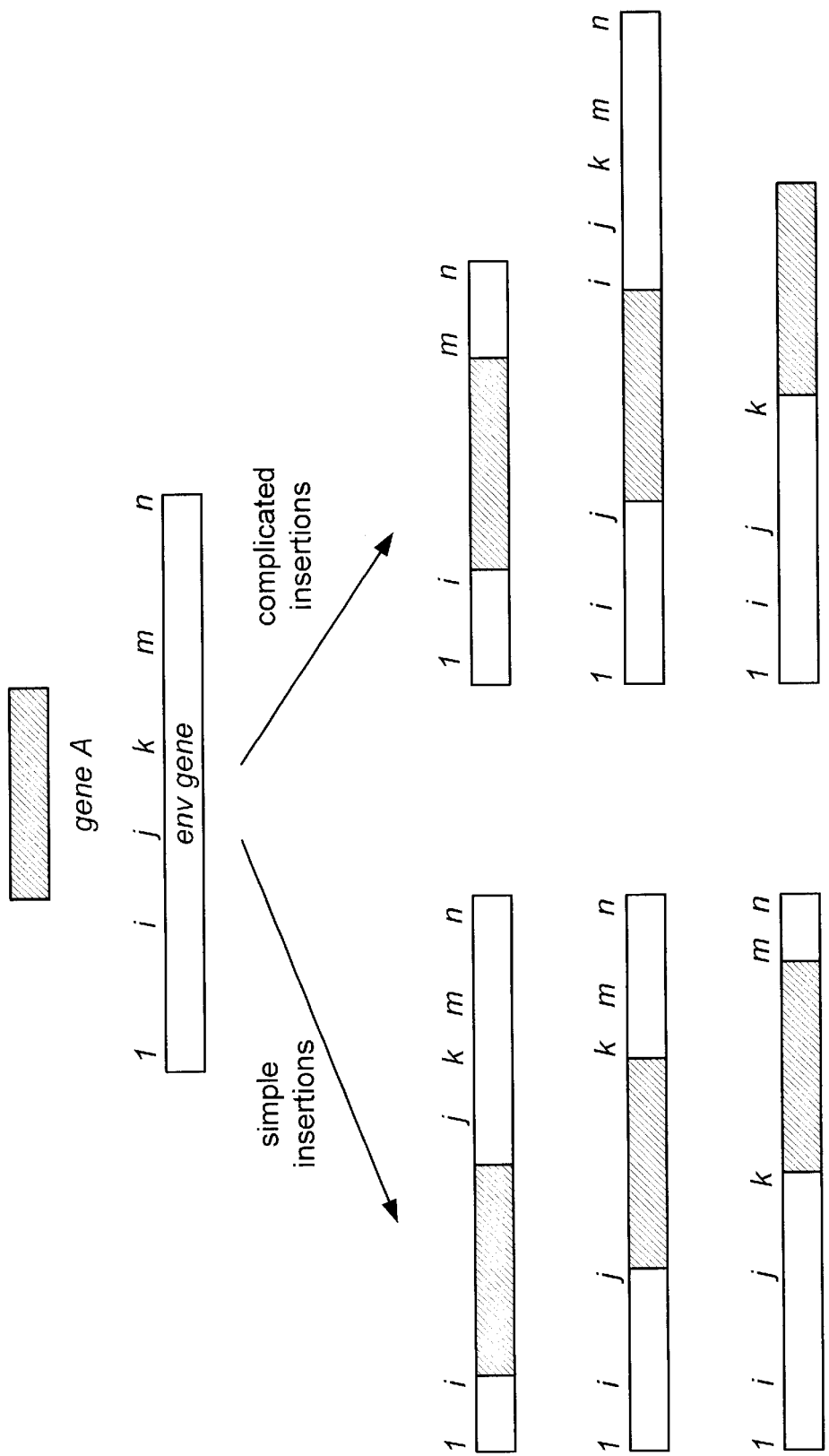
FIG. 1 shows a sample permuted, chimeric retroviral env library where the nucleic acid insert is represented by "gene A."

The present invention provides methods of making libraries of permuted, chimeric nucleic acids, in which a second, typically heterologous, nucleic acid is inserted at random into the target permuted sequence. This assembly process yields a combinatorial library composed of two types of permuted, chimeric genes: one population with simple, random insertions, and a second population that contains more complex deletions, duplications, and substitutions (see FIG. 1). These libraries allows quick and efficient assembly of permuted, chimeric nucleic acid libraries that encode proteins with novel functions or provide nucleic acids such as promoters with novel function. A further advantage of the system is that the first nucleic acid is permuted over the length of the sequence from about one to about twenty nucleotides, preferably about one to ten nucleic acids, most preferably about one to about five nucleic acids, providing a comprehensive array of chimeric molecules.

The selected nucleic acid used to make the permuted arms can be any suitable nucleic acid from, e.g., a mammal, a human, a virus, a bacteria, a plant, a eukaryote, or a prokaryote. Examples of selected nucleic acids include retroviral proteins such as env and integrase; adenoviral proteins such as the fiber protein; tissue, temporal and developmentally specific promoters; enzymes; chemokines, cytokines, and growth factors; ligands such as c-kit, Il-2, Il-3, Il-6, IGF-I, IGF-II, INF-γ, FGF, TGF, TNF-α, TNF-β, NGF, BDNF, CNTF, flt31, and protein A.

In one embodiment, permuted, chimeric env genes are constructed and used to make a targeted retroviral vector. The insertion of a second nucleic acid, e.g., a domain from another ligand protein, into the env gene alters the specificity of the env gene and allows targeting of the env protein to specific cell types. For example, a retroviral vector expressing the targeted env protein is capable of transducing a reporter or therapeutic gene into a specifically targeted cell such as a cancer cell, an HIV infected cell, an antigen presenting cell, e.g., a macrophage or a dendritic cell, or a pluripotent hematopoietic stem cell. One goal of this retroviral-based gene therapy strategy is that the retrovirus is restricted in the range of cells it can infect, so as to decrease the probability of occurrence of adverse events such as insertional mutagenesis. Furthermore, it is desirable to target retroviral vectors to cells that normally would be resistant to transduction by the vector.

Using the methods described herein, one can construct a chimeric retrovirus with a manipulated envelope protein that recognizes particular cell-surface molecule present on the chosen target cells. Such an env gene includes the domain of a ligand protein, which recognizes a receptor present on the target cell, e.g., c-kit, I1-2, I1-3, I1-6, IGF-I, IGF-II, INF-γ, FGF, TGF, TNF-α, TNF-β, NGF, BDNP, CNTF, flt31, and protein A. In addition, nucleic acids encoding random peptide sequences can be used to create chimeric env genes that recognize unknown cell receptors, or immunoglobulin family cell receptors such as the TCR, MHC class I molecule, and MHC class II molecule. Nucleic acid sequences for such ligand molecules are typically publicly available on databases such as GenBank, while random primers can be synthesized using automated DNA synthesis.

Env sequences can be derived from any known retrovirus, including, e.g., HIV, MuLV, SMRV, SFV, HPV, MMTV, SRVs, HTLV-I, HTLV-II, BLV, BIV, SIV, visna virus, EIAV, FIV, and EIAV, and from any of the retroviral subfamilies, e.g., Oncovirinae, Lentivirinae, or Spumavirinae. Many retroviral clones, including HIV-1 clones, are well characterized and available. Well-established repositories of HIV (and other retroviral) sequence information include GenBank, EMBL, DDBJ and the NCBI. Well characterized HIV-1 clones include HXCB2, HIV-1-MN and HIV-1-MN-ST.1 (See, e.g., Hall, et al., *J. Virol.*, 66(9):5553–5560 (1992)).

In one embodiment, env genes from a wild-type retrovirus that does not normally infect a human or other cell type used for screening a chimeric env, e.g., murine, human or primate cells affords an ideal background against which targeted transduction can be demonstrated, e.g., ecotropic murine leukemia virus (MLV) env (rat and murine cells only), feline immunodeficiency virus (FIV) env (feline cells only), or avian spleen necrosis virus (SNV) env (bird cells only). In addition, other env genes from retroviruses that have the ability to infect specific mammalian cell types can be used to create targeted retroviruses, e.g., HIV-1 env, HIV-2 env, HTLV-1 env, HTLV-2 env, human foamy virus (HFV) env, and amphotropic MLV env.

In another embodiment, genes from other viruses besides retroviruses can be used to create targeted vectors. For example, the ligands that mediate adenovirus and adeno-associated virus transduction, such as the adenovirus fiber protein, can be manipulated using the methods of the invention to create permuted, chimeric genes that specifically target adenovirus and adeno-associated virus vectors. Such chimeric genes are screened as described above for their ability to transduce target cells.

Furthermore, the methods of the invention can be applied to creating proteins with new or additional activities. For example, the specificity of a retroviral integrase gene can be altered by creating a permuted, chimeric integrase gene that includes inserts from yeast transposon TY3. TY3 preferentially inserts into pol II transcribed genes within 1–2 basepairs of integration (Dildine et al., *J. Virol.* 72:4297 (1998)). Such chimeric proteins can be screened for their ability to integrate into a new, site specific position. In addition, the specificity of proteases and other enzymes can be altered by inserting domains from other proteins.

Finally, the specificity of promoters such as the LTR can be altered so that they respond to tissue-specific, temporal, and developmental-specific transcription factors, e.g., a STAT binding site found in promoters that are responsive to cytokine signalling. In one example, a chimeric LTR library is screened by cloning the permuted, chimeric LTR library into a retroviral vector containing a reporter gene, so that the reporter gene is driven by the chimeric LTR. The library is transfected into a retroviral packaging cell, and the retroviral genome containing the chimeric LTR operably linked to the reporter gene is packaged into a retrovirus particle. Infected target cell clones are screened for expression of the reporter gene or responsiveness of the reporter gene to activation by various signalling pathways.

II. Definitions

For purposes of the present invention, the following terms are defined below.

A "selected nucleic acid" refers to any nucleic acid of choice, e.g., a gene, cDNA, promoter, transcribed region, protein coding region and the like, that forms the basis for a permuted nucleic acid library. The selected nucleic acid can represent a cis-acting nucleic acid sequence, or encode an RNA or a protein. The selected nucleic acid can be any useful nucleic acid from any suitable species, e.g., a mammal, a human, a virus, a plant, a bacteria, etc. Typically, the selected nucleic acid is permuted into "5' arms," which represent the 5' end of the selected nucleic acid, and "3' arms," which represent the 3' end of the selected nucleic acid, e.g., the 5' end of an env gene and the 3' end of an env gene.

A "permuted nucleic acid library" refers to a collection of nucleic acids derived from a selected nucleic acid. Each pennuted nucleic acid in the library differs from another permuted nucleic acid in the library by processive alterations of the selected nucleic acid. The alteration can be at the 5' or the 3' end of the molecule, or at both ends. The library therefore contains a collection of individual nucleic acids that typically are permuted over the length of the selected nucleic acid by about 1–50 nucleotides, preferably about 1–10 nucleotides, most preferably about 1–5 nucleotides. A "permuted nucleic acid" refers to a nucleic acid from the permuted nucleic acid library. Typically, the permuted nucleic acids are provided by randomly, enzymatically digested a selected nucleic acid, e.g, by exonuclease digestion or by DNAse digestion.

A "permuted, chimeric nucleic acid" is an artificially constructed nucleic acid comprising a 5' arm of a permuted, selected nucleic acid, a nucleic acid insert, and a 3' arm of a permuted, selected nucleic acid. Preferably, the nucleic acid insert is heterologous with respect to the arms of the selected nucleic acid. Optionally, the nucleic acid insert is also permuted.

A "backbone nucleic acid" refers to any nucleic acid comprising a selected nucleic acid. For exonuclease digestion, the backbone nucleic acid has at least one exonuclease sensitive site, e.g., a single-stranded nick or gap in a double-stranded, circular molecule, an internal single-stranded nick or gap in a double-stranded linear molecule, or at least one exonuclease sensitive end of a double-stranded linear molecule. The backbone nucleic acid can be provided, e.g., by restriction digestion of a plasmid at one or more restriction sites; by amplification, e.g., with PCR optionally followed by restriction digest; by reverse transcription optionally followed by restriction digest; by automated synthesis; by nicking a double-stranded circular plasmid with DNase I in the presence of $Mg^{2+}$; or by creating a gaped double stranded plasmid by extending a primer annealed to a single stranded plasmid, and the like according to well known methodology. For DNase I digestion, the backbone nucleic acid can either be linear or circular.

A "nucleic acid insert" refers to the nucleic acid that is inserted between 5' and 3' permuted nucleic acid arms to create a "permuted, chimeric nucleic acid." Preferably, the nucleic acid insert is heterologous with respect to the permuted nucleic acid, although non-heterologous nucleic acids can also be used in the methods of the invention.

"Bilateral digestion" refers to exonuclease digestion that proceeds from both ends of a backbone nucleic acid.

"Unilateral digestion" refers to exonuclease digestion that proceeds from only one end of a backbone nucleic acid.

An "exonuclease sensitive site" is a site on the end of a nucleic acid that can be digested by exonuclease, e.g., the end of a linear double-stranded molecule with a 5' overhang or a single-stranded nick or gap in a double-stranded circular plasmid.

An "exonuclease resistant site" is a site on the end of a nucleic acid that cannot be digested by exonuclease, e.g., a 3' overhang of about 4 nucleotides or more produced by an enzyme such as Pst I or Sph I.

A "monomerization restriction site" is a restriction site that, when digested, provides complementary ends for re-ligation or re-sealing of a linear nucleic acid.

The term "heterologous" when used with reference to a nucleic acid indicates that the nucleic acid comprises two or more subsequences which are not found in the same relationship to each other in nature. For instance, the nucleic acid is typically recombinantly produced, having two or more sequences from unrelated genes or from a wild type gene a mutated version of the gene arranged to make a new functional nucleic acid. For example, in one embodiment, a sequence from a protein A gene is heterologous with reference to an env sequence when the two sequences are placed in a relationship other than the naturally occurring relationship of the nucleic acids.

A "vector" is a composition which can transduce, transform, infect or otherwise transfer nucleic acid into a cell, thereby causing the cell to replicate or to express nucleic acids and/or proteins other than those native to the cell, or in a manner not native to the cell. A vector includes a nucleic acid (ordinarily RNA or DNA) to be expressed and/or replicated by the cell. A vector optionally includes materials to aid in achieving entry of the nucleic acid into the cell, such as a viral particle, liposome, protein coating or the like. The term vector encompasses DNA and RNA, plasmids, expression vectors, viral vectors and the like. A vector can be a prokaryotic or a eukaryotic vector.

A virus or vector "transduces" a cell when it transfers nucleic acid into the cell. A cell is "transformed" by a nucleic acid when a nucleic acid transduced into the cell becomes stably replicated by the cell, either by incorporation of the nucleic acid into the cellular genome, or by episomal replication.

"Nucleic acid" refers to deoxyribonucleotides or ribonucleotides and polymers thereof in either single- or double-stranded form. Unless specifically limited, the term encompasses nucleic acids containing known analogues (synthetic and naturally occurring) of nucleotides, which have similar binding properties as the reference nucleic acid and are metabolized in a manner similar to the reference nucleotides. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, and mRNA, and polynucleotide.

A "primer" or "oligonucleotide" is a nucleic acid capable of binding to a target complementary nucleic acid sequence, i.e., a "primer sequence." As used herein, a primer may include natural (i.e., A, G, C, or T) or modified bases (7-deazaguanosine, inosine, etc.). The bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. The primers are optionally labeled ligands such as with biotin to which a streptavidin complex may later bind, for affinity purification of a nucleic acid that has incorporated the labeled primer.

An "adapter" is an oligonucleotide that is incorporated onto the end of a nucleic acid, e.g., by ligation or PCR. Typically the adapter provides sequence such as a restriction site or a primer sequence.

An "interior" primer sequence refers to a primer sequence that is at the 3' end of a 5' arm, the 5' end of a 3' arm, and the 5' end and 3' end of a nucleic acid insert. Conversely, an "exterior" primer sequence refers to a primer sequence that is at the 5' end of the 5' arm and the 3' end of the 3' arm. The terms exterior and interior refer to the position of the primer sequences after assembly of the permuted, chimeric nucleic acid (see FIG. 8).

"Amplification' or "amplifying" includes reactions such as PCR, LCR, reverse transcription, splice overlap extension, pull-through splice overlap extension and the like.

"Cells" that comprise vectors and libraries of the invention include both prokaryotic and eukaryotic cells.

III. Constructing a Library of Permuted Nucleic Acids

The libraries of the present invention are constructed by first making libraries of permuted, selected nucleic acids. After construction of the permuted nucleic acids, these nucleic acids may be used immediately to make a permuted, chimeric nucleic acid library by the addition of the nucleic acid insertion. Alternatively, the permuted nucleic acids can be ligated into vectors and later used to generate a number of permuted, chimeric nucleic acids libraries. When the permuted nucleic acids are ligated into vectors (either new vectors, or re-sealed plasmids) they typically contain "universal" sequences for the addition of nucleic acid inserts. Typically, two libraries of permuted nucleic acids are made, which correspond respectively to the 5' arm and the 3' arm of the selected nucleic acid.

The permuted nucleic acids are randomly truncated an arbitrary distance from the 5' or 3' end of the selected nucleic acid. These permuted nucleic acids are constructed so that they contain unique, defined sequences at the ends of the molecules, for further use in chimeric library construction, or for subcloning into vectors.

The first step in generation of the library is the permutation step. The permutation reaction is preferably performed with an exonuclease digest. However, alternative methods of permutation can also be used, e.g., by digestion with DNase I and $Mn^{2+}$ to produce double-stranded breaks. The method of digestion, exonuclease, DNase I, or otherwise, is titrated according to standard methodology to yield incubation times that give the appropriate amount of permutation (see Example I). For example, the exonuclease reactions typically permute about 1–20, preferably about 1–10, most preferably about 1–5 nucleotides over the entire sequence of the gene. Similarly, DNase digestions are titrated so that the selected nucleic acid is digested about 1–2 times per molecule, resulting in a permutation similar to that found in the exonuclease reactions.

Exonuclease reactions are preferably performed on a linear nucleic acid; alternatively, a circular nucleic acid with a single-stranded nick or gap can be used for exonuclease digestion. DNase digestions can be performed using either a linear or a circular nucleic acid. For exonuclease reactions, a plasmid containing the selected gene is typically linearized by digestion with a restriction enzyme that creates an exonuclease sensitive site. The restriction site may be upstream of, downstream of, or within the selected nucleic acid. The plasmid can be digested with one or more restriction enzymes or nicked with DNase I and $Mg^{2+}$. Alternatively, a linear nucleic acid can be provided by PCR amplification, with exonuclease sensitive sites on the ends of the molecule, by reverse transcription, by enzymatic DNA synthesis, or by automated DNA synthesis, and other methods well known to those of skill in the art.

Figure 5:
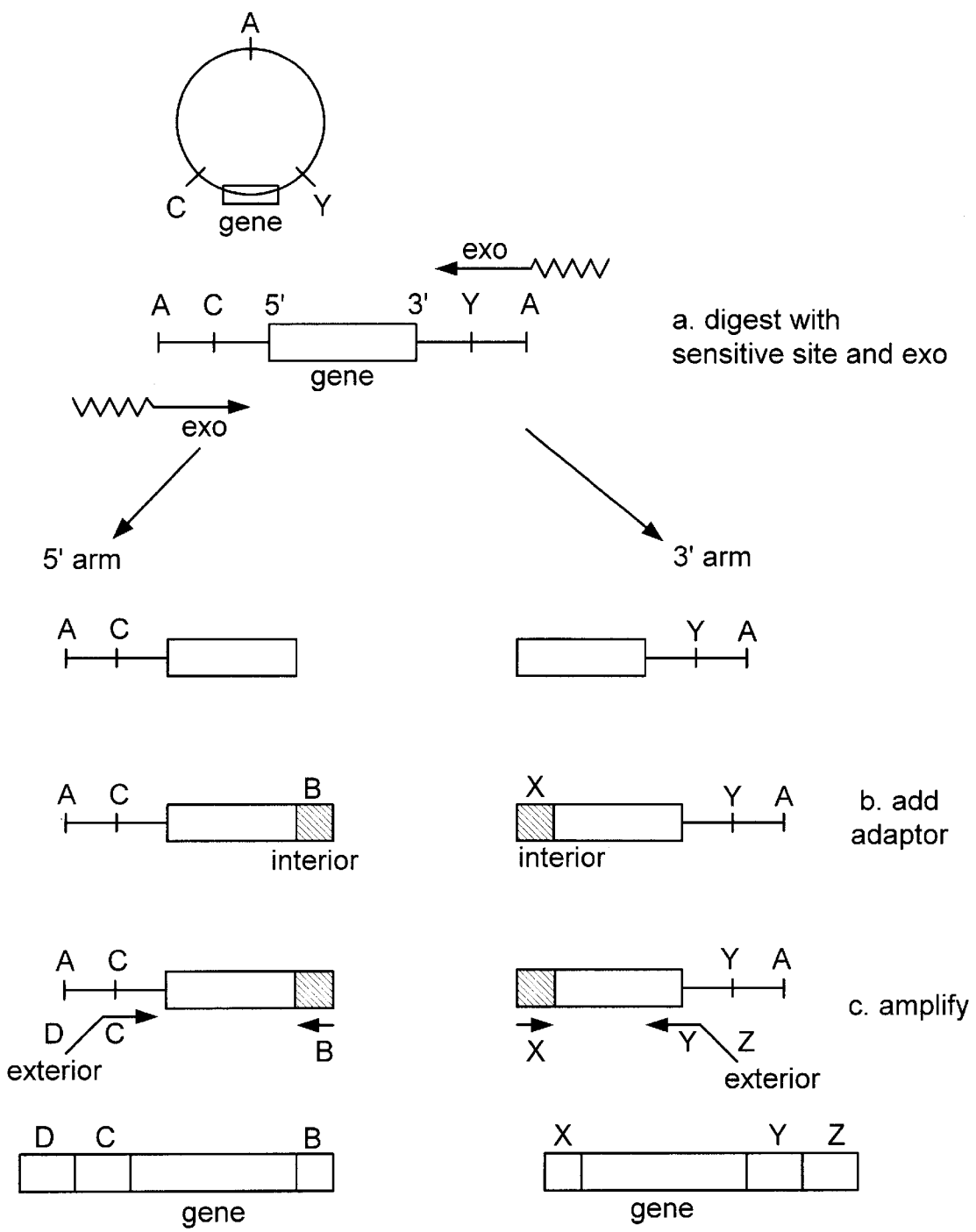
FIG. 5 shows one embodiment of a method for producing 5' and 3' permuted nucleic acids by bilateral exonuclease digestion.
Figure 6:
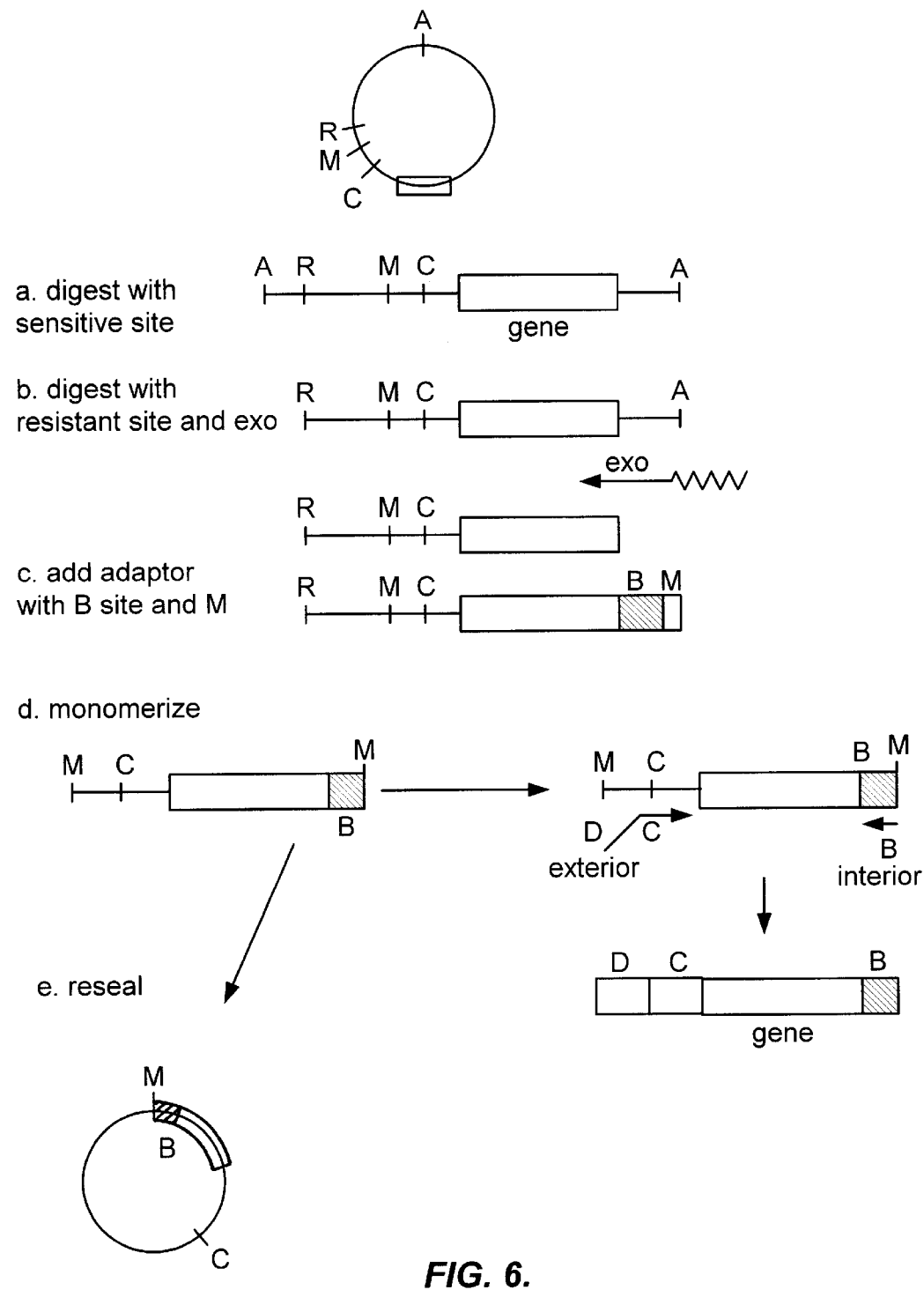
FIG. 6 shows one embodiment of a method for producing 5' permuted nucleic acids using unilateral exonuclease digestion.
Figure 7:
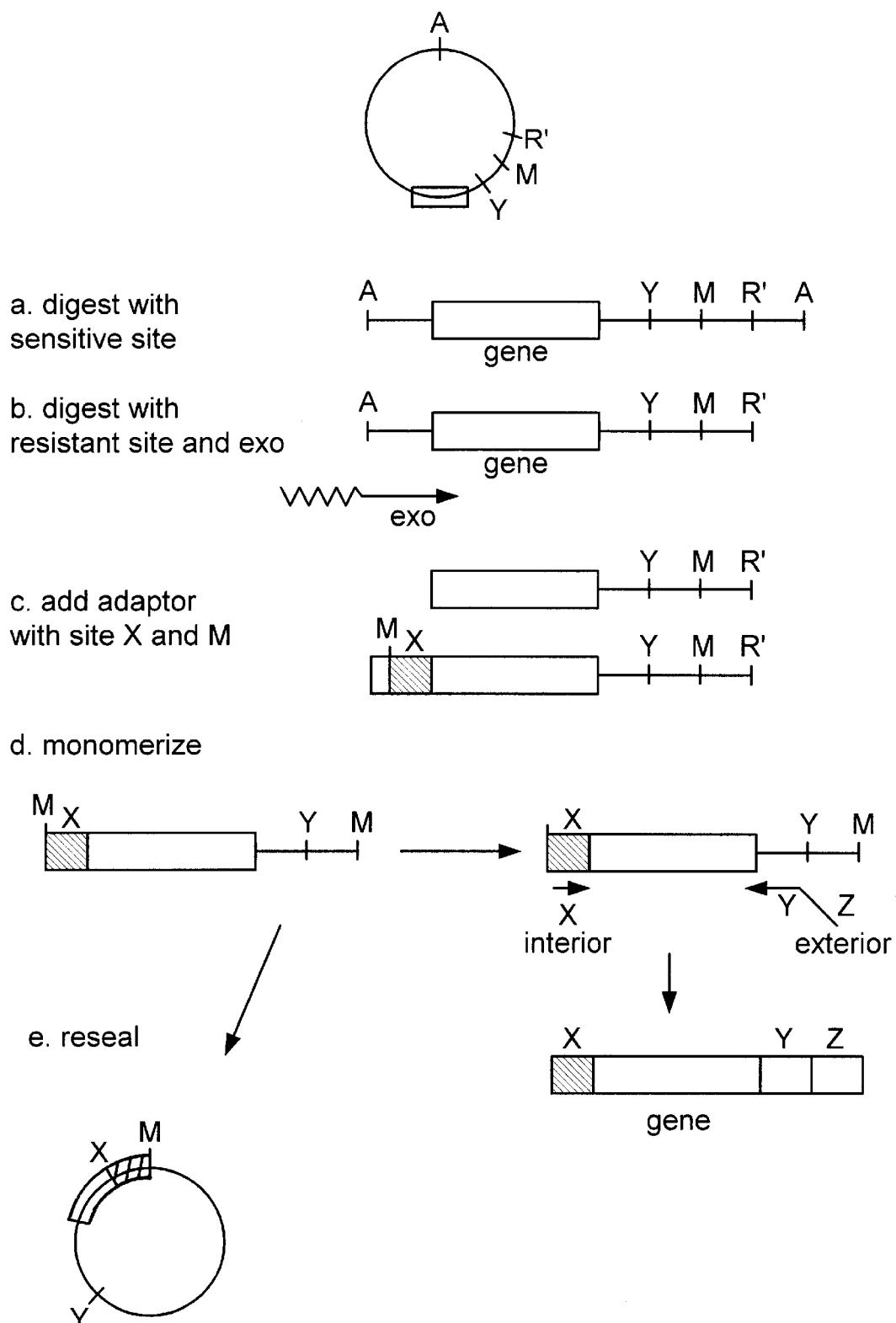
FIG. 7 shows one embodiment of a method for producing 3' permuted nucleic acids using unilateral exonuclease digestion.

The exonuclease digestion can be either unilateral or bilateral and performed according to methods known to those of skill in the art (see FIGS. 5–7) (see, e.g., Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994); see also Clark & Henikoff, "Ordered Deletions Using Exonuclease III," chapter 12, *Methods in Molecular Biology*, volume 57, *In Vitro Mutagenesis Protocols* (1996)). For bilateral digestions, the backbone nucleic acid, e.g., with exonuclease sensitive sites on both ends, is digested and the exonuclease digestion is performed according to standard methodology (see FIG. 5). For unilateral digestions, one end or site of the backbone nucleic acid has an exonuclease resistant site, so that digestion can only proceed from one end (see FIGS. 6–7) (Henikoff, *Gene* 28:351–359 (1984)).

Any suitable exonuclease can be used for the reaction, e.g., *E. coli* exonuclease III (double-stranded 3'-5' activity) or 17 gene 6 or lambda exonuclease (double stranded 5'-3' activity). As described above, the extent of exonuclease digestion is titrated and controlled by variables such as temperature, ionic strength, and duration. Preferably, the digestions are calibrated for $Na^+$ concentration and enzyme/template ratios, and then incubated for equally spaced time points (see Example I, below). The reaction is terminated, e.g., with a buffer containing zinc.

The exonuclease strategy is one embodiment of a method producing a permuted set of truncation products, or arms. An alternative method for achieving the same result would be digesting a DNA template with DNase I in the presence of a $Mn^{2+}$ cofactor (rather than the standard $Mg^{2+}$ cofactor) at an empirically determined DNase to template ratio. The $Mn^{2+}$ permits the DNase to cut both strands of the template (as opposed to nicking only a single strand in the presence of $Mg^{2+}$). Under conditions where a given plasmid is cut one or a few times, preferably about two times, one could then polish the plasmid fragment ends and then link on the linkers as described below. This reaction creates a deletion at a random site within the selected nucleic acid of interest. This DNAse based method, does not require pooling of the truncation products—the entire range of "effective deletions" for a given arm would be generated in a single reaction.

After termination of the exonuclease or DNase I reaction, if necessary time points are pooled and ends of the DNA are clipped and polished, e.g., with a single-stranded nuclease (e.g., S1 or Mung bean) and Klenow or T4 pol treatment. A number of commercially available kits contain exonuclease, reaction buffers, single-stranded nuclease and polymerase enzymes, e.g., Promega's ERASE-A-BASE® kit, NEB's EXO-SIZE™ kit, etc.

After the ends of the permuted fragments have been polished to render them double stranded, the ends are ligated to an oligonucleotide adapter. Before ligation to the adapter, the bilateral exo digestion is typically divided into two parts, one part for formation of the 5' arm and one part for formation of the 3' arm. The unilateral reactions already have been designated as 5' or 3' arm reactions depending on the position of the exonuclease sensitive site relative to the selected nucleic acid. Typically, the adapter is hemiphosphorylated, to facilitate ligation of the adapter in the appropriate orientation. The adapter includes a unique "interior" primer sequence, for amplification. The adapter optionally includes a unique restriction site for directional subcloning. The adapter also optionally includes a spacer region, which encodes in frame, small amino acids (see FIGS. 5–7).

The adapter may also include a monomerization restriction site. The monomerization restriction site functions to provide complementary ends (with a second monomerization site flanking the permuted nucleic acid in the plasmid DNA) for "re-sealing" of the digested plasmid containing the selected (now permuted) nucleic acid. The monomerization restriction site also permits digestion of the ligated adapter so that the permuted nucleic acid has only one adapter sequence in the proper orientation. The monomerization restriction site is preferably used in unilateral digestion reactions (see FIGS. 6–7).

Once the adapter oligonucleotides have been ligated to the permuted nucleic acids, the permuted nucleic acids can be used in a variety of ways. If the permuted nucleic acid has monomerization restriction sites, the nucleic acid can be digested with the appropriate enzyme, and then re-ligated or "re-sealed" to provide a plasmid or vector library of permuted nucleic acids (see FIGS. 6–7). The permuted nucleic acids can also be rescued by amplification prior to subcloning into a vector or addition of the nucleic acid insert. The amplification "rescue" of the arms typically uses primers complementary to the "interior" primer sequence provided by the adapter and a primer complementary to the opposite end of the molecule (see FIGS. 5–7). The second primer sequence typically flanks the selected nucleic acid, providing amplification of nucleic acids that are truncated either at the 5' or the 3' end of the selected nucleic acid. Use of the second primer sequence at one end or the other end of the gene designates a bilateral digestion reaction as either 5' or 3'. The second primer sequence is used to incorporate the "exterior" primer sequence, which is not originally a part of the starting nucleic acid material. Amplification or PCR rescue offers the advantages of removing a materials constraint and providing precise delineation of permuted nucleic acid ends.

After amplification rescue, e.g., by PCR, the arms are preferably purified by affinity purification before further manipulation. The affinity purification is performed by first incorporating a label into the amplification primers. The label is one that has affinity for a receptor, e.g., biotin/streptavidin, protein A/immunoglobulin, histidinelantihistidine antibody, and the like. After amplification and preferably after affinity purification, the 5' and 3' arms are subcloned into vectors for propagation as libraries, or are directly used to make a chimeric nucleic acid library. A permuted nucleic acid library thus contains a population of selected molecules that are permuted over the sequence of the nucleic acid and bounded by defined sequences.

For sub-cloning and propagation of a permuted nucleic acid arm library, the particular vector used to transport the genetic information into a cell is not particularly critical. Suitable bacterial vectors are well known in the art and described, e.g., in Sambrook et al. and Ausubel et al. Bacterial vector systems are available in, e.g., *E. coli, Bacillus sp.*, and Salmonella (Palva et al., *Gene* 22:229–235 (1983); Mosbach et al., *Nature* 302:543–545 (1983). Kits for such systems are also commercially available. Eukaryotic vectors for mammalian cells, yeast, and insect cells are well known in the art and are also commercially available. Any of the conventional vectors used for expression or replication in eukaryotic or prokaryotic cells may be used. Standard bacterial vectors include plasmids such as pBR322 based plasmids, Bluescript, pSKF, and pET23D, and bacteriophages, e.g., lambda and M13 based vectors. Exemplary eukaryotic vectors include pMSG, pAV009/A⁺, pMTO10/A⁺, pMAMneo-5, baculovirus pDSVE, and vectors allowing expression of genes under the direction of the SV40 early promoter, SV40 later promoter, metallothionein promoter, MuLV LTR, murine mammary tumor virus promoter, Rous sarcoma virus promoter, polyhedrin promoter, or other promoters shown effective for expression in eukaryotic cells.

The elements that are typically included in vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to transduce bacterial, mammalian, yeast or insect cell lines. Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983). Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra).

IV. Constructing a Library of Permuted, Chimeric Nucleic Acids

After the permuted 5' and 3' arms have been obtained, they are typically used to create a chimeric library with a nucleic acid insert of choice (see FIG. 1). The nucleic acid insert can be generated by simple exonuclease digestion and adapter ligation to produce permuted inserts. The nucleic acid insert can also be generated by PCR with random primers, or it can represent a known, fixed sequence, e.g., a protein domain. Alternatively, random oligonucleotides can be inserted between the 5' and 3' permuted arms. Standard techniques for isolating nucleic acid inserts are well known to those of skill in the art.

Figure 8:
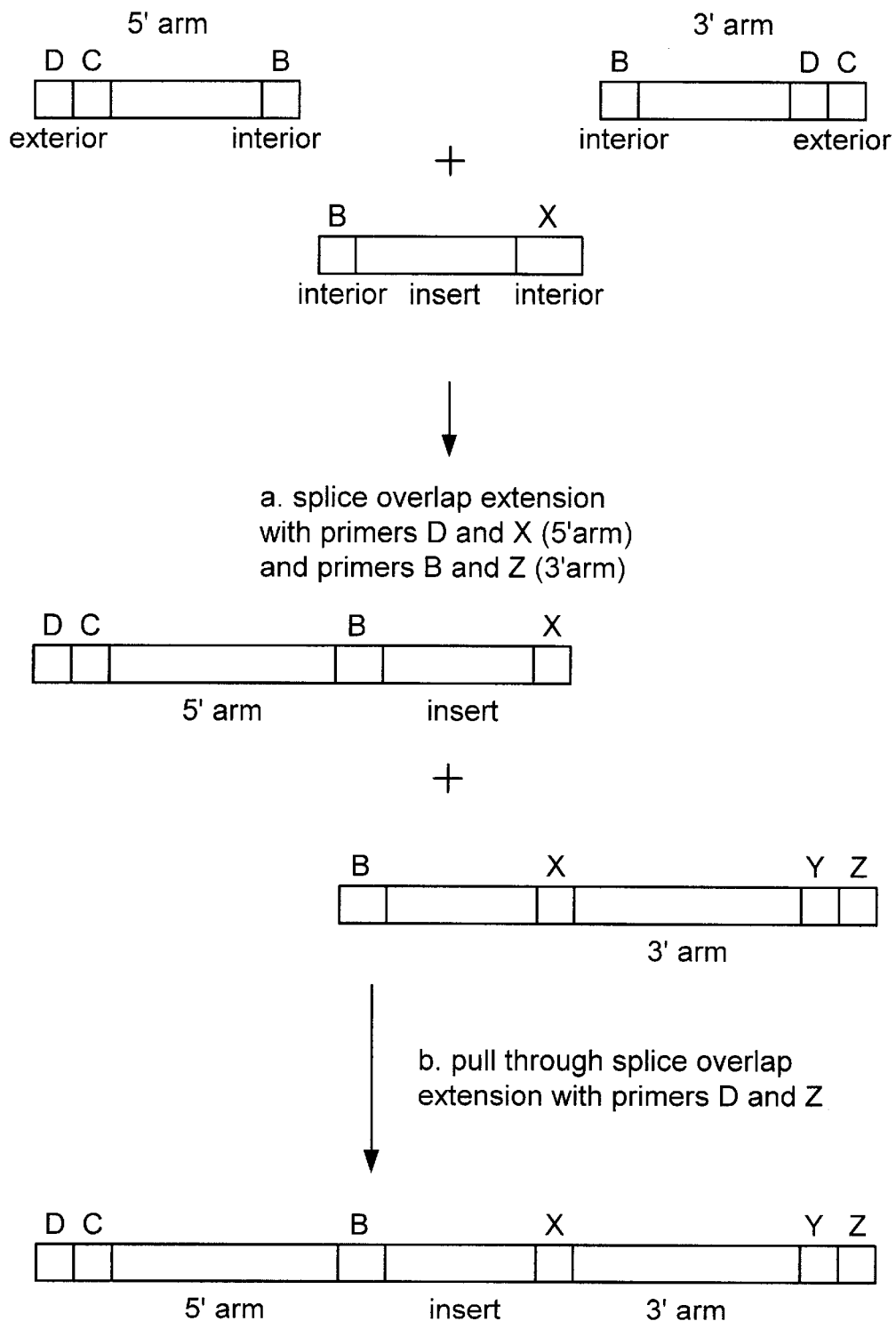
FIG. 8 shows one embodiment of assembly of permuted nucleic acids and nucleic acid inserts into a permuted, chimeric nucleic acid library.

The nucleic acid insert has adapters that am correspond to the interior primer sequences at the 3' end of the 5' arm and at the 5' end of the 3' arm, respectively (see FIG. 8). The adapters are added to the insert according to standard methodology, e.g., ligation or PCR. These adapters are used to ligate the insert between the arms, and/or to amplify the insert.

The interior adapter sequences on the insert allow ligation to or hybridization to the interior adapter sequences on the 5' and 3' arms. The adapters can be directly ligated to the arms and then amplified. Preferably, the adapters are allowed to anneal to the arms (without ligation), and then individual 5' or 3' arm-insert nucleic acids are amplified using splice overlap extension with one exterior and one interior primer (see Example I and FIG. 8; Horton, In Vitro Recombination and Mutagenesis of DNA: SOEing Together Tailor-Made Genes," chapter 25, *Methods in Molecular Biology*, volume 15, *PCR Protocols* (White, ed., 1993)). In addition or in the alternative, exterior primers can be used for "pull-through" splice overlap extension amplification, to amplify 5' arm-insert-3' arm nucleic acids (see FIG. 8). A library assembled in this manner is then subcloned into the desired expression, screening or propagation vectors using any standard subcloning strategies. The permuted, chimeric nucleic acid library assembled in this manner contains 5' and 3' permuted nucleic acids from a selected gene, into which a nucleic acid (preferably heterologous) has been randomly inserted. The permuted, chimeric nucleic acid is further bounded by known sequences, e.g., primer sites.

Alternatively, the arms and inserts can be assembled using methodology such as traditional restriction enzyme-ligation methods; T/A or blunt ended PCR cloning strategies; or ligase free methods based on T4 pol 3'-5/exo generated or uracil N-glycosidase generated overhangs.

V. How to Screen for Functional Permuted and Chimeric Genes

The permuted, chimeric products of the libraries described above can be screened by a variety of methods. For example, targeted vectors can be screened for their ability to infect specific cell types. For such screening methods, vectors are constructed that express a selectable marker after successful transduction of a target cell. The target cells are screened for marker expression, and chimeras rescued, e.g., by PCR amplification. Promoter mutations can be screened for their ability to promote expression upon exposure to signaling molecules or other specific conditions. The promoter is typically operably linked to a genetic marker, which allows identification and rescue of the functional chimeric promoter. Proteins such as integrases are screened for activity using a marker attached to the retroviral genome, which also expresses the chimeric integrase gene. Finally, enzymes and other proteins with altered function are screened by expression and an appropriate functional assay.

Figure 2:
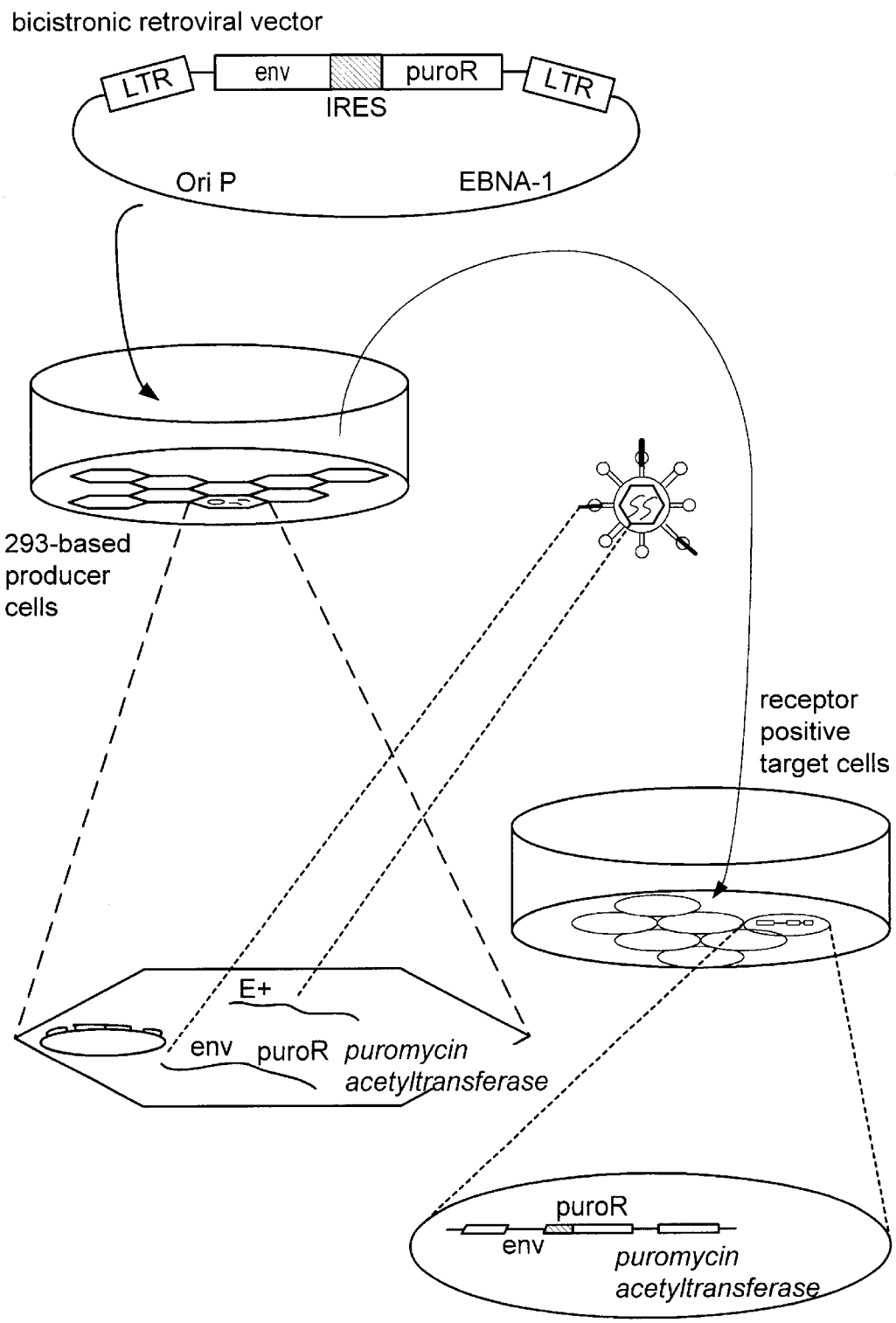
FIG. 2 shows a bicistronic retroviral genome and a schematic of a screening method for a permuted, chimeric env gene. A bicistronic retroviral genome is constructed that contains the genes for both a chimeric env protein and a gene encoding a genetic marker separated by an internal ribosome entry site (IRES) sequence. Transfection of the retroviral genome DNA into viral packaging cells yields RNA transcripts that are packaged into infectious particles (as viral genomes) and are also translated in the packaging cells to produce a chimeric env protein, which is expressed on the surface of the resulting packaged retroviral particles. The retroviral particles expressing the chimeric env protein infect target cells, where the genetic marker is expressed from the viral genome, allowing selection of functional chimeric env genes. The chimeric env genes are then rescued by PCR amplification.
Figure 4:
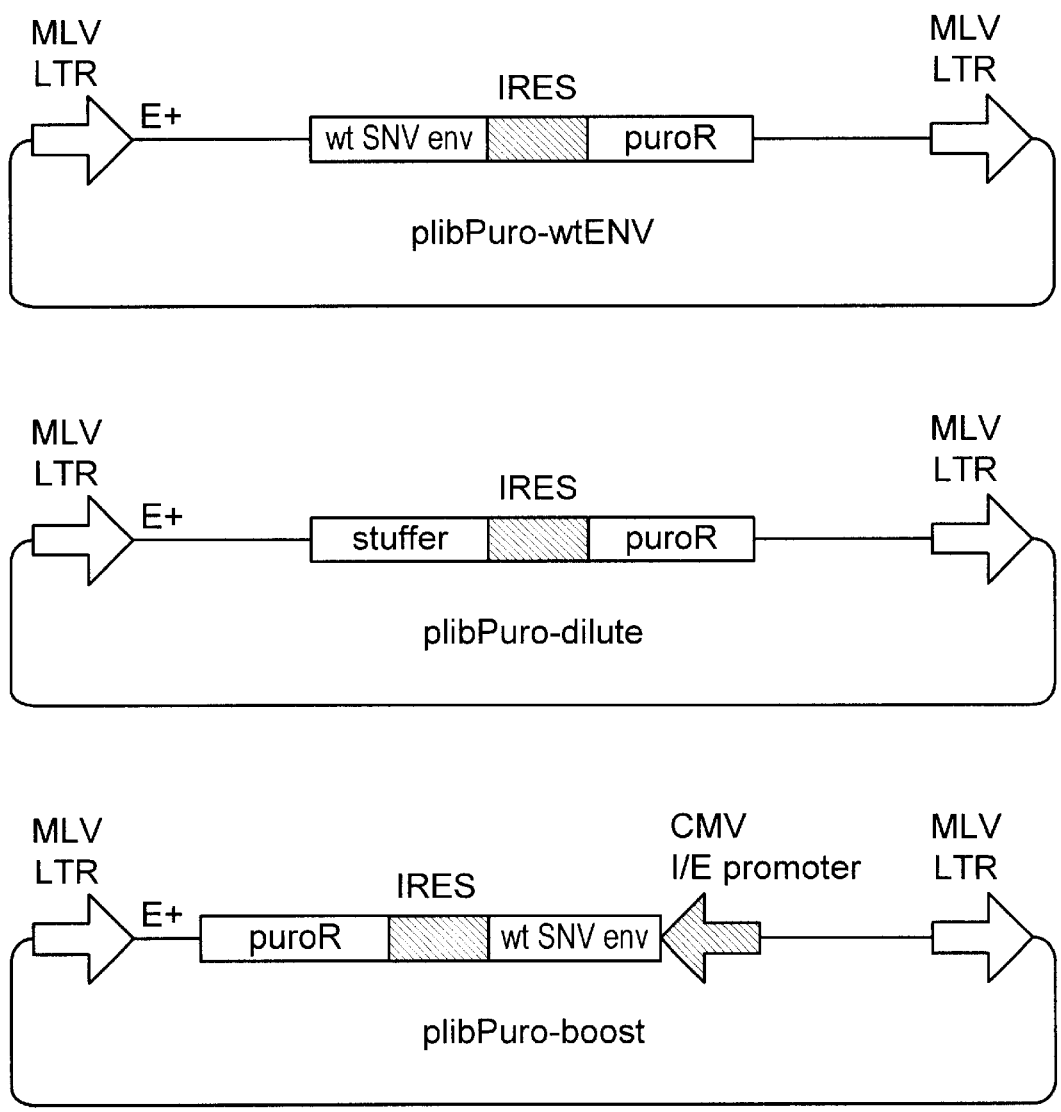
FIG. 4 shows an example of bicistronic vectors for expressing and screening for chimeric env genes.

In one example, a screening method for a permuted, chimeric env protein relies upon the fact that the genes of a retroviral genome are expressed in both the viral packaging (producer) cells and within the target cells transduced by the virus. A bicistronic retroviral vector is constructed with a genetic marker for retroviral-mediated transduction (e.g. an antibiotic resistance marker) physically linked to a gene encoding a chineric env protein (FIGS. 2 and 4). These retroviral vectors contain an IRES element, which permits expression of two genes, the chimeric env gene and the antibiotic resistance gene, from a single RNA transcript that represents the retroviral genome. This vector design permits linkage of a selectable marker to the env gene responsible for successful infection of the target cells. The chimeric gene responsible for successful infection can be rescued from the integrated provirus in the transduced and selected target cells.

Figure 3:
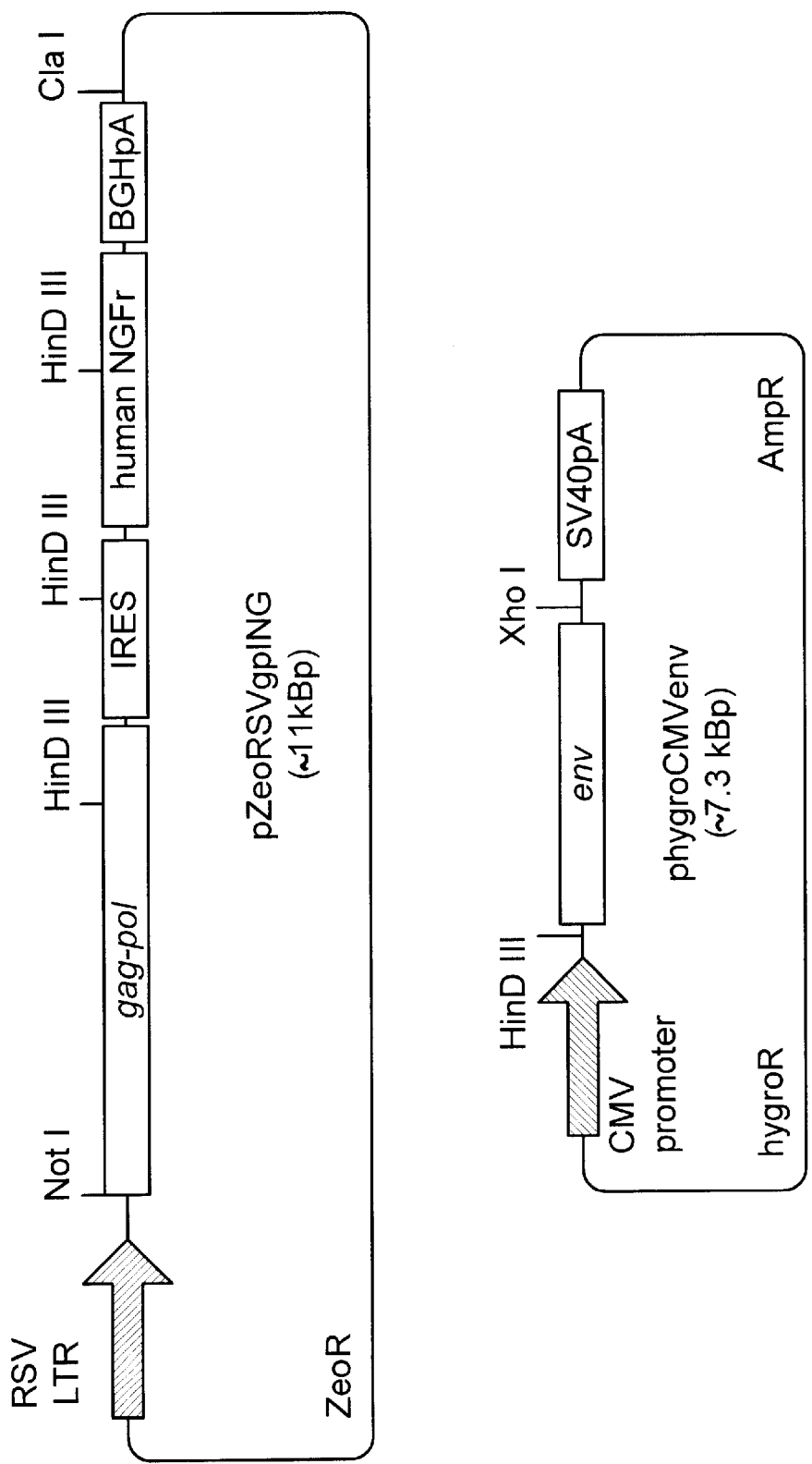
FIG. 3 shows an example of plasmids used to create retroviral packaging cells.

"Packaging" or "producer" cells help replication-deficient retroviral vectors, which may lack viral protein coding sequences that have been replaced by an expression cassette, to form virus particles that are capable of infecting another host cell. Packaging cells often contain retroviral mutations so that they cannot supply wild type retrovirus genomes to produce infective particles; their activity is usually limited to complementing the replication-deficient retroviral vector and to producing infective virus particles (see FIG. 3).

Expression of the chimeric env protein in the producer cells leads to formation of virions with the chimeric env protein. These virions bearing chimeric env-ligand proteins, which are competent to bind a specific receptor, will specifically transduce the target cells. In addition, the genetic marker with the resistance gene is expressed from the transduced retroviral genome. The chimeric env virions may or may not also include wild type env proteins supplied by the producer cells. Producer cells that lack wild type env genes can be used when only chimeric env genes are desired in the retroviral vector.

After transduction, target cells are screened for expression of the genetic marker, e.g., by drug resistance. Drug resistant colonies contain the provirus, which has both the gene for the resistance marker and the chimeric env gene, which mediated transduction of the target cell. The chimeric env gene can then be rescued, e.g., by PCR or other suitable techniques. One embodiment of a screening method is outlined below in Example II.

Once a functional chimeric env gene has been identified and rescued, it is cloned into an appropriate vector and used to create packaging cells. This is done by transducing the packaging cell line used to package a retroviral genome (containing a therapeutic gene of choice) with the selected chimeric env gene. These packaging cells are used to produce retroviral vectors that display the chimeric env gene. The retroviral vectors are then used to deliver selected genes and proteins to target cells, e.g., cancer cells, HIV infected cells, antigen presenting cells and the like. The targeted retroviral vectors contain genes for gene therapy and treatment of diseases such as cancer, or deliver antigens to antigen presenting cells for production of cytotoxic T lymphocyte vaccines against diseases such as cancer and HIV infection.

Retrovirus packaging cells have been developed as a safe and efficient method of producing retroviral particles (see Miller, *Hum. Gene Ther.* 1: 5–14 (1990)). Typically, packaging cells contain a mutated retrovirus that produces in trans the proteins necessary for formation of a viral particle. However, the packaging cells do not themselves produce packagable retrovirus RNA genomes because they contain retrovirus sequences from which the ψ site has been deleted. Thus, replication deficient retrovirus RNA containing therapeutic genes can be introduced into cells for packaging into retrovirus particles.

Many cell types are suitable for the creation of a packaging cell line, for example, HeLa cells and NIH 3T3 cells. The mutated retrovirus used to make the cell line can be present in many forms, for example, the viral genes encoding the viral capsid components may be separated on different plasmids (Markowitz et al., *Virology* 167: 400–406 (1988)). The cell line PA317 is one example of a typical cell line used to package retroviral vectors (Miller & Buttimore, *Mol. Cell. Biol.* 6: 2895–2902 (1986)).

Suitable methods know to those skilled in the art are used to harvest the packaged retrovirus cassette from packaging cell lines (see generally Bunnell & Morgan, Retrovirus-Mediated Gene Transfer, in *Viral Genome Methods*, pp. 3–23 (Adolph ed., 1996)). Generally, after introduction of the chimeric env gene, the packaging cells are incubated under standard cell culture conditions to allow packaging of the retrovirus cassette and budding of viral particles into the cell supernatant. The cell supernatant is then collected after a suitable amount of time, e.g., after 24 hours. The supernatant is then frozen or used immediately.

VI. Targeted Gene Therapy

In one embodiment, the present invention provides methods of making chimeric genes for targeting viral vectors to specific cells. These chimeric genes, e.g., retroviral env and adenoviral fiber protein, are expressed in packaging cells to create targeted vectors. The targeted viral vectors are used to deliver nucleic acids to specific cells for gene therapy and vaccine production.

In one preferred class of embodiments, the chimeric genes are used to create targeted viral vectors for gene therapy. Gene therapy provides methods for combating chronic infectious diseases such as HIV, as well as non-infectious diseases such as cancer and birth defects such as enzyme deficiencies. For example, Yu et al. (1994) *Gene Therapy* 1:13–26 provide a general guide to gene therapy strategies for HIV infection (see also, Sodoski et al. PCT/US91/04335). One general limitation of common gene therapy vectors such as murine retroviruses is that they only infect actively dividing cells, and they are generally non-specific. The present invention provides chimeric genes such as env genes that allow one of skill to generate powerful viral gene therapy vectors that specifically target cells such as cancer cells and stem cells in vivo and in vitro. In addition to retroviruses, other targeted viral vectors such as adenoviral vectors can be developed using chimeric fiber protein genes produced by the methods of the invention.

A therapeutic gene typically uses a promoter such as a retroviral LTR sequence for expression. In addition to the LTR, other suitable promoters can be used to express the therapeutic gene. Constitutive promoters for directing expression of therapeutic nucleic acids are also preferred, such as pol III promoters. In one example, PCT application PCT/US94/05700 (WO 94/26877) and Chatterjee et al. (*Science* (1992), 258: 1485–1488) describe anti-sense inhibition of HIV-1 using a constitutive pol III expression cassette expressing anti-TAR RNA. Chatterjee et al. (PCT application PCT/US91/03440 (1991)) describe AAV-based vectors that express antisense TAR sequences. PCT publication WO 94/26877 (PCT/US94/05700) describes a variety of gene therapy strategies, including the use of suicide genes, trans-dominant genes, ribozymes, anti-sense genes, and decoy genes in gene therapy vectors.

Ex vivo methods for introducing a therapeutic gene into a cell involve transducing the cell ex vivo with viral vectors expressing chimeric genes of this invention, and introducing the cell into the organism. Target cells include antigen presenting cells and stem cells isolated or cultured from a patient and the like. See, e.g., Freshney et al., supra and the references cited therein for a discussion of how to isolate and culture cells from patients. Alternatively, the cells can be those stored in a cell bank (e.g., a blood bank). In one class of embodiments, the therapeutic gene encodes a therapeutic agent (e.g., suicide gene, trans-dominant gene, ribozyme, anti-sense gene, or decoy gene) under the control of an activated or constitutive promoter.

In one preferred embodiment, stem cells are used in ex vivo procedures for cell transformation and gene therapy. The advantage to using stem cells is that they can be differentiated into other cell types in vitro, or can be introduced into a mammal (such as the donor of the cells) where they will engraft in the bone marrow. Methods for differentiating CD34$^+$ cells in vitro into clinically important immune cell types using cytokines such a GM-CSF, IFN-γ and TNF-β are known (see, Inaba et al. (1992) *J. Exp. Med.* 176, 1693–1702, and Szabolcs et al. (1995) 154: 5851–5861). An affinity column isolation procedure can be used to isolate cells which bind to CD34, or to antibodies bound to CD34. See, Ho et al. (1995) *Stem Cells* 13 (suppl. 3): 100–105. See also, Brenner (1993) *Journal of Hematotherapy* 2: 7–17. In another embodiment, hematopoietic stem cells are isolated from fetal cord blood. Yu et al. (1995) *PNAS* 92: 699–703 describe a preferred method of transducing CD34$^+$ cells from human fetal cord blood using retroviral vectors. Rather than using stem cells, T cells are also transduced in preferred embodiments in ex vivo procedures. Several techniques are known for isolating T cells. In one method, Ficoll-Hypaque density gradient centrifugation is used to separate PBMC from red blood cells and neutrophils according to established procedures. Cells are washed with modified AIM-V (which consists or AIM-V (GIBCO) with 2 mM glutamine, 10 µg/ml gentamicin sulfate, 50 µg/ml streptomycin) supplemented with 1% fetal bovine serum (FBS). Enrichment for T cells is performed by negative or positive selection with appropriate monoclonal antibodies coupled to columns or magnetic beads according to standard techniques. An aliquot of cells is analyzed for desired cell surface phenotype (e.g., CD4, CD8, CD3, CD14, etc.).

In general, the expression of surface markers facilitates identification and purification of target cells such as stem cells, cancer cells, HIV-infected cells, antigen presenting cells, and the like. Methods of identification and isolation of cells include FACS, column chromatography, panning with magnetic beads, western blots, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. For a review of immunological and immunoassay procedures in general, see Stites and Terr (eds.) 1991 *Basic and Clinical Immunology* (7th ed.) and Paul supra. For a discussion of how to make antibodies to selected antigens see, e.g. Coligan (1991) Current Protocols in Immunology Wiley/Greene, NY; and Harlow and Lane (1989) *Antibodies: A Laboratory Manual* Cold Spring Harbor Press, NY; Stites et al. (eds.) Basic and Clinical Immunology (4th ed.)

In addition to the ex vivo uses described above, the viral vectors expressing chimeric genes of the invention are useful generally in cloning methods. Viral vectors expressing chimeric genes are used to deliver a selected gene to a targeted cell in vitro or in vivo. This provides one of skill with a technique and vectors for transforming specific cells with a nucleic acid of choice, e.g., in drug discovery assays, or as a tool in the study of gene regulation, or as a general cloning vector.

Viral particles containing therapeutic nucleic acids can be administered directly to the organism for transduction of cells in iWvo. Administration is by any of the routes normally used for introducing a molecule into ultimate contact with blood or tissue cells. Viral vectors expressing chimeric genes are used target cells for the treatment and prevention of diseases such as AIDS in animals and human patients. The viral vectors are administered in any suitable manner, preferably with pharmaceutically acceptable carriers. Suitable methods of administering such packaged nucleic acids in the context of the present invention to a patient are available, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

The viral vectors expressing chiimeric genes, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration and intravenous administration are the preferred methods of administration. The formulations of packaged nucleic acid can be presented in unit-dose or multi-dose sealed containers, such as ampules and vials.

Cells transduced by the targeted viral vectors as described above in the context of ex vivo therapy can also be administered intravenously or parenterally as described above.

The dose administered to a patient, in the context of the present invention should be sufficient to effect a beneficial therapeutic response in the patient over time, or to inhibit infection by a pathogen. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of diseases such as AIDS or cancer, the physician evaluates circulating plasma levels, vector toxicities, progression of the disease, and the production of anti-vector antibodies. The vectors of this invention can supplement treatment of disease conditions by any known conventional therapy, including cytotoxic agents, nucleotide analogues and biologic response modifiers.

For administration, viral vectors and transduced cells of the present invention can be administered at a rate determined by the LD-50 of the vector or transduced cell type, and the side-effects of the vector or cell type at various concentrations, as applied to the mass and overall health of the patient. Administration can be accomplished via single or divided doses.

For introduction of transduced cells, prior to infusion, blood samples are obtained and saved for analysis. Between $1 \times 10^8$ and $1 \times 10^{12}$ transduced cells are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion are repeated every 2 to 3 months for a total of 4 to 6 treatments in a one year period. After the first treatment, infusions can be performed on a outpatient basis at the discretion of the clinician. If the reinfusion is given as an outpatient, the participant is monitored for at least 4, and preferably 8 hours following the therapy.

Transduced cells are prepared for reinfusion according to established methods. See, Abrahamsen et al. (1991) *J. Clin. Apheresis* 6:48–53; Carter et al. (1988) *J. Clin. Arpheresis* 4:113–117; Aebersold et al. (1988), *J. Immunol. Methods* 112: 1–7; Muul et al. (1987) *J. Immunol. Methods* 101:171–181 and Carter et al. (1987) *Transfusion* 27:362–365. After a period of about 2–4 weeks in culture, the cells should number between $1 \times 10^8$ and $1 \times 10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

If a patient undergoing infusion of a vector or transduced cell develops fevers, chills, or muscle aches, he/she receives the appropriate dose of aspirin, ibuprofen or acetaminophen. Patients who experience reactions to the infusion such as fever, muscle aches, and chills are premedicated 30 minutes prior to the future infusions with either aspirin, acetaminophen, or diphenhydramine. Meperidine is used for more severe chills and muscle aches that do not quickly respond to antipyretics and antihistamines. Cell infusion is slowed or discontinued depending upon the severity of the reaction.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Construction of a Permuted, Chimeric env Library

To model the process of shuffling a ligand domain into an env gene, a system was selected based upon the MLV ecotropic env gene. Briefly, the strategy was to shuffle a 416 bp "mock" ligand domain, from a region of the MLV ecotropic env gene that encodes a protein domain responsible for the tropism of the virus (termed the host-determining region, or HDR), back into an HDRdeleted MLV env template.

Two other features of the model system are of importance. First, the HDR domain to be shuffled was "marked," using site-directed mutagenesis, with a silent HinD III restriction site ($A_{413}$->T) within the MLV open reading frame (note: numbering convention is that the A residue of the start ATG for env is number +1). This mutation would thus enable differentiattion, by simple restriction digest, of a recombinant DNA molecule generated by this combinatorial strategy from a wild-type DNA molecule that escaped through the genetic screen.

Second, this marked HDR domain was not shuffled across the entire HDR-deleted MLV gene, but only over the front half of the HDR-deleted gene. The front half of the HDR-deleted gene extended from a site in the 5' untranslated region (UTR) of the cDNA, about 370 bases upstream of the start codon, to the unique Bam HI site in the deleted gene at nucleotide position 343 (corresponding to position 760 in the wild-type HDR gene). This particular model system was selected so that at least one member of the combinatorial library would possess biological activity (e.g., is encoded by the reconstituted gene in which the marked HDR domain was reinserted in register) and differ from wild type only by the presence of the HD3 restriction marker.

A. Preparation of HDR-deleted env Starting Material

A 5' region of the MLV cDNA was subcloned into pBluescript plasmids to perform mutagenesis on the MLV ORF and to arrange cDNA with the unique flanking restriction sites (e.g., eliminate some confounding Bam HI sites in the starting MLV env plasmid and render the Bam HI site at position 760 in the env gene unique). The resulting HDR-deleted env gene was used to create library of permuted env genes.

SOE PCR was used to splice together two fragments of the MLV env gene, yielding a net deletion of a 416 bp fragment encoding a portion of the HDR domain (between bases 163 and 578 of the MLV env ORF). This HDR-deleted env gene fragment was recloned into a pBluescript derivative, which then served as the template DNA for the exonuclease reactions which would generate the permuted env gene "arms".

A variation of SOE PCR using mutagenic primers was performed to introduce a silent HD3 site at nucleotide 423 of the MLV env ORF. This mutated env ORF was subcloned back into an pBluescript vector derivative, yielding a template which in a PCR could generate a marked HDR-domain for the combinatorial library assembly reactions.

To delete the HDR domain, two separate PCR amplifications were performed using ecotropic MLV env cDNA as template: one with primer pair T3 (5'-d(AAT TAA CCC TCA CTA AAG GG)-3') SEQ ID NO:1 and RV-SOE#1 (5'-d(TGT GAT ATC TCC ATT GGT TAC)-3'), SEQ ID NO:2 and one with primer pair RV-SOE#2 (5'-d(GTA ACC AAT GGA GAT ATC ACA GTA AAC AAC AAT CTC ACC)-3') SEQ ID NO:3 and BHI (5'-d(GTG GGA TCC CAA ATG TAA GCC CTG)-3') SEQ ID NO:4. The first primer set amplified a 663 bp fragment containing 398 bases upstream of and the first 162 base pairs within the MLV env ORF, while the second primer set amplified a 205 bp fragment encompassing bases 579 to 764, inclusive, of the MLV env ORF. These two PCR products were cross annealed and extended so that the resulting DNA fragment was amplified by splice overlap extension (SOE) PCR, using primers T3 and BHI, to yield a 853 bp product. This product corresponds to an MLV env gene lacking bases 163–578 in the open reading frame. It was cut with Bam HI and subcloned into pBluescript II $SK^+$ to yield pBS-HDRDRV#5.

A pBluescript II $SK^+$ derivative was generated, in which the unique Bam HI site was destroyed by digesting with Bam HI, filling with Klenow, and religating to seal the blunted plasmid, to yield pBSDB#6. The deleted amino terminal domain of the MLV env gene was recovered as an Eco RI flanked fragment, which was subcloned into the unique Eco RI site of pBSDB#6, yielding the constructs pT3-DHDR and pT7-DHDR, in which the amino domain is sense relative to the bacteriophage T3 or T7 RNA polymerase promoters, respectively. pT3-DHDR served as the template plasmid for generating the permuted env gene fragments required in the library assembly.

To create the marked HDR domain, the first 761 bases of the MLV ecotropic env gene, along with 398 bases of proviral DNA upstream of the env start codon were subcloned as an Eco RI—Bam HI flanked fragment from pBS-MLV5 into pBluescript II $SK^+$ to yield pBS-Env(r→b).

Plasmid pBS-MLV5 was used as a template in a PCR based mutagenesis procedure, in which a silent mutation was introduced into coding region of the amino terminal domain of the MLV env gene at base 413 creating a HinD III restriction site, while maintaining the wild type $L_{105}$ amino acid residue. Briefly, two separate PCR amplifications were performed using either the primers T3 (5'-d(AAT TAA CCC TCA CTA AAG GG)-3') SEQ ID NO:1 and HD3mut (5'-d(GAG TTG TCT GGT CAA GCT TGA GTC TGT TC)-3'), SEQ ID NO:5 or primers BstEIImut (5'-d(CCT GGG AGG TAC CCA ATG GAG ATC GG)-3') SEQ ID NO:6 and BHI (5'-d(GTG GGA TCC CAA ATG TAA GCC CTG)-3') SEQ ID NO:4. The T3 and HD3mut primers yielded a 921 bp product, which contained the desired HinD III mutation, while the BstEII and BHI primers yielded a 629 bp product in which the BspEII site present in the wild type env gene was mutated. The two PCR products were cross annealed, and the resultant templates amplified by SOE PCR, using primers T3 and BHI, to yield a 1262 bp product. The product was then cut with BstEII and Bam HI, and the resultant 620 bp band subcloned into same sites of pBS-Env(r→b) to yield pBS-HDR/HD3.

B. Permuted env Gene generation

Exonuclease treatments and fragment polishing reactions were performed using mix and match components from Promega's ERASE-A-BASE® System and other suppliers as noted.

pT3-DHDR served as the template plasmid for generating the permuted env gene fragments. First, ~30 μg of plasmid was linearized by restriction digest with a restriction enzyme that generated an exo sensitive DNA end, by cleaving in the vector polylinker either upstream or downstream of the cDNA. Twelve μg of linearized plasmid (from either linearization reaction) in μL was added to 35 μL of 10× exo III buffer (ProMega Kit; 660 mM Tris-HCl, pH 8.0; 6.6 mM MgCl$_2$) and 313 μL of water. This mixture was distributed into seven 45 μL aliquots.

To the first 45 μL aliquot, 84.5 U of exo III (BRL, 1.3 μL) was added, and the reaction mixed thoroughly and maintained at ambient temperature. Two μL of this reaction mix was dispensed into a microtiter plate well containing 6 μL of Exo Stop Buffer/S1 Nuclease mix (Promega Kit; 40 mM KOAc, pH 4.6; 270 mM NaCl; 1.35 mM ZnSO$_4$, 7% glycerol, 0.3 U/μL of S1 nuclease). After 5 seconds, a second 2 μL aliquot was dispensed from the exo reaction into a second microtiter plate well containing 6 μL of Stop/S1 buffer, and so forth. Dispensing continued at 5 sec. intervals until the first 45 μL reaction was exhausted. The total elapsed time between the start of the first exo reaction (i.e., enzyme addition) and the last dispensing was noted (in the above reaction, total elapsed time ~105 sec.). The second 45 μL exo digestion was set up as before, and the reaction allowed to proceed at ambient temperature for about 95 sec. before dispensing of the first 2 μL into stop/S1 buffer as before. This particular delay gave a few overlapping/duplicate time points with the first series of aliquots. Repeated dispensing at 5 sec. intervals was performed as before until the second reaction was exhausted. The second 45 μL exo reaction was used to span exo digestion time points between 95 sec. and ~200 sec. This staggered start and collection procedure was repeated for the remaining five 45 μl aliquots. As the batch of exo III had been calibrated previously under these conditions to digest at a rate of about 100 bp/min. or 1.6 bp/sec., the entire reaction series generated from the seven starting 45 μL aliquots should give, on average, permuted species with deletions encompassing zero to ~700 bases total, and with the average difference in deletion length between the neighboring 5 sec. time points being about 6–8 bases.

At the completion of the seven sets of reactions, the microtiter plates containing the ~140 separate S1 reactions were moved to room temperature and S1 digestion allowed to proceed for 30 minutes. The individual reactions were then recombined back into 7 pools, such that reactions 1–20 constituted pool 1, reactions 21–40 constituted pool 2, and so forth. To these seven pools, 1/10 volume of S1 stop buffer was added (300 mM Tris-base and 50 mM EDTA) and the reactions precipitated using 0.3 vol of 7.5 M NH$_4$OAc and 2 vol. of EtOH in the presence of 20 μg of glycogen. The pellets were washed with 70% EtOH, dried, and resuspended in 9 μL of water. Klenow buffer was added to give a final solution of 20 mM Tris-HCl, pH 8.0, and 100 mM MgCl$_2$. The reaction was brought to 37° C., and then 0.2 U of Klenow was added per reaction. The reactions were incubated for 3 min., at which time dNTPs were added to a final concentration of 10 μM, and the reactions allowed to incubate 5 additional minutes. The Klenow polishing reaction was terminated by heat inactivation of the enzyme (65° C. or 70° C. for 10 min.)

Additionally, similar reactions were performed using the above procedure, except that 30 sec. time-points were taken from a single starting exo reaction, to span a deletion series from time zero to about 12 minutes post-exo addition. Deletion products generated from the plasmid linearized from a site downstream of the cDNA were collective by referred to as "left" arms, while deletion products generated from the plasmid linearized from a site upstream of the cDNA were collective referred to as "right" arms.

Exo reaction conditions may be also varied with respect to NaCl concentrations, as an alternative to temperature regulation of digestion activity and rate. General guidelines for varying exonuclease reaction parameters can be found in Eun, *Enzymology Primer for Recombinant DNA Technology*, pp 215–225 (1996).

C. Linker Ligation

Truncated, permuted DNAs generated and polished in the manner described above were ligated to oligonucleotide duplex linkers in a series of parallel ligation reactions as follows. At the end of the Klenow inactivation treatment, reactions were cooled on ice, and 40 μL of ligation mix was added to each reaction. Ligation mix contained 50 mM Tris-HCl, pH 7.6; 10 mM MgCl$_2$, 1 mM ATP, 5% PEG, 1 mM DTT, ~3 U T4 DNA ligase, and about a 100× excess of duplex oligonucleotide linker. Note that the sequence of the duplex linkers differs between the left arm reactions and the right arm reactions (see the linker set below for specific sequences). Ligations were incubated overnight at 14° C., and then digested with monomerization enzyme corresponding to the restriction site present in the specific left arm or right arm oligonucleotide linker. An additional restriction endonuclease digestion was performed simultaneously or sequentially (depending upon the buffer compatibility with that required for the monomerization reaction) with the monomerization reaction. The enzyme selected for this additional digest corresponded to a site present near the termini of the cDNA in the starting vector, but interior to the sites selected for initial plasmid vector linearization reaction. The rationale for this additional digest was to cleave away linkers ligated to cDNA fragments associated with "background" undeleted molecules (i.e., cDNA fragments upon which the exo had not reacted during the cDNA truncation steps).

At the completion of the monomerization and "background-reduction" restriction endonuclease digestions, the endonucleases were heat-inactivated or the reaction products EtOH precipitated and resuspended. The ligation/monomerization reaction products were passed through a spin column 2× to separate unlinked linkers and linker digestion fragments away from the intact cDNA arms.

D. PCR "Rescue" of Arms.

The separate arms from the various reactions were rescued in four parallel PCRs (narrowed down to four pools from the seven pools described above, termed pools L1 through L4 and R1 through R4) using an arm specific set of primers, one primer which was 5'-biotinylated and complementary to the linker site added during the ligation above (interior terminus primer), and a second primer complementary to the ends of the MLV env cDNA in the template vector (exterior terminus primer). Standard PCR reactions (2 mM MgCl$_2$, Taq DNA pol, BRL 1×PCR buffer, 1 μM primers, 10:1 ratio of Taq DNA pol/Pwo DNA pol; 50 μL PCR reaction) were performed. This "exo-rescue PCR" yielded products in which one strand of the given arm was biotinylated at its 5' end (at the interior primer site) and in which this interior sequence terminates precisely at the end of the C sequence from the starting linker (i.e. no additional bases of the M site are appended to the product). The PCR products also contained a sequence present at the exterior terminus which was unique to the PCR product (it was not present in the starting template of the arm). In this way, the exo-rescue PCR reactions prepared arms with precisely delineated and unique termini, and which could be purified away from the remainder of the PCR reaction components, including template, using biotin-(strep)avidin based technologies.

In this example, ProMega Streptavidin MagnaSphere Paramagnetic Particles were used to bind the biotinylated PCR products. Binding, washing and eluting were performed according to manufacturer's instructions. Briefly, 200 μL of beads were washed 3× with 300 μL of 0.5×SSC, followed by capturing of the beads against the side of the tube between washes using a magnetic stand. After removal of the final wash buffer, 30 μL of the exo-rescue PCR containing biotinylated products was added to 11.25 μL of 20×SSC and 408.75 μL of water (final SSC, 0.5×), and the entire 450 μL added to the bead pellet. Mixing of contents was achieved by finger-flicking, the mixture was incubated at ambient temperature for 15 min., and the beads then captured by magnetic stand as before. The supernatant was removed carefully, and the beads washed again 4× with 300 μL of 0.1×SSC. After the last wash, the bead pellet was resuspended in 100 μL of water.

E. Preparation of Marked HDR Ligand Fragment

One ng of plasmid template pBS-HDRDRV#5 was placed into a standard PCR cocktail (2 mM MgCl$_2$, Taq DNA pol, BRL 1×PCR buffer, 1 μM primers, 10:1 ratio of Taq DNA pol:Pwo DNA pol; 50 μL PCR reaction) and a marked HDR domain amplified using the ligand D and ligand E primers. The resulting 416 bp fragment was then gel purified and served as the model ligand domain for the combinatorial assembly steps, below.

F. Combinatorial Library Assembly

Five μL of the bead solution from a specific right or left arm exo rescue PCR was mixed with 2 μL of purified, marked HDR PCR product (about 2 ng) and these 7 μL of templates were mixed into a standard PCR reaction (2 mM MgCl$_2$, Taq DNA pol, BRL 1×PCR buffer, 1 μM primers, 10:1 ratio of Taq DNA pol:Pwo DNA pol; 50 μL PCR reaction). Left arm-HDR SOE products were amplified using the left exterior exo-rescue primer and a biotinylated ligand E primer, while HDR-right arm SOE products were amplified using the right exterior exo-rescue primer and a biotinylated ligand D primer. The biotinylated PCR products from the hemi-SOE reactions were purified exactly as described above for the exo-rescue PCR products.

Left arm hemi-SOE products so purified (2.5 μL) were mixed with purified right arm hemi-SOE products (2.5 μL) and the resulting 5 μL of template transferred to a SOE PCR cocktail (2 mM MgCl$_2$, Taq DNA pol, BRL 1×PCR buffer, 1 μM primers, 10:1 ratio of Taq DNA pol:Pwo DNA pol; 50 μL PCR reaction) containing the SOE pull through primer pair (left SOE pull through and right SOE pull through primers). The resulting SOE products represent a combinatorially assembled library of test molecules, with the diversity of molecules in any given SOE PCR depending upon the diversity of the left and right arm hemi-SOE templates added into the SOE PCR. The SOE products were then digested with Sph I and Bam HI, and cloned into the same sites of the acceptor library screening vector, pBiPuroDHDR254 (described below).

The positive selection (e.g., biotin purification) steps are advantageous for avoiding regeneration of a large amount of unmutated products at the SOE steps. The hemi-SOE steps also provide products possessing a very large overlap for the final SOE assembly step.

G. Retroviral Screening Vector Construction

An MLV retroviral vector was created: 1) by insertion of an encephalomyocarditis virus internal ribosome entry site (IRES) upstream of the puromycin resistance gene; 2) by insertion of a multiple cloning site polylinker upstream of the IRES; and 3) by cloning of a truncated ecotropic MLV env gene, encoding amino acid residues 235–665, within the polylinker region upstream of the IRES-puro cassette.

The resulting vector, pBiPuroDHDR254, was used to clone the permuted, chimeric library inserts; and was used to express a single, bicistronic RNA transcript that was translated to two separate protein products, a candidate chimeric env protein and the puromycin resistance protein.

pBiPuroDHDR254 was created as follows: The starting plasmid, plasmid pBiPuro, was derived from a bicistronic MLV retroviral vector, pGIP. The GFP gene, upstream of an IRES element and puromycin N-acetyltransferase gene, was deleted from pGIP and replaced by an duplex oligonucleotide linker containing various restriction endonuclease sites to yield pBiPuro.

pBiEnvDHDR254 was derived from pBiPuro, described above. The primers 5'-d(AGA TCC CCT TGG TTT ACC)-3' SEQ ID NO:7 and 5'-d(GCG CGG CCG CTC GAG CTA TGG CTC GTA CTC TAT AGG)-3' SEQ ID NO:8 were used to the amplify terminal 191 bases of the MLV ecotropic env gene from a pBluescript vector derivative containing the MLV eco env gene (pB-HIT8). The second primer introduces a Xho I restriction site immediately downstream of the env gene stop codon. This PCR product was digested with Cla I and Xho I and subcloned into the same sites of pB-HIT8, to yield pB-HIT8D3'B. The 5' leader region, along with the first 761 bases of the env coding sequence were removed from pB-HIT8D3'B by digesting with Bam HI, purifying away the 1.15 kBp fragment containing the 5' portion of the MLV env gene, and resealing the vector backbone to yield pB-HIT8D5'B.

A short oligonucleotide linker was cloned into the unique Bam HI site of pBiPuro, converting it into a Sph I site and yielding pBiPuro(Sph). Similarly, a short oligonucleotide linker was cloned into the unique Xba I site of pB-HIT8D5'B, converting it to a Sph I site and yielding pBS-MLV(Sph). The 1239 bases encoding the carboxy terminal amino acids of the MLV ecotropic env gene were then obtained as a Sph I—Xho I flanked fragment from pBS-MLV8D5'B, which was subcloned into the same sites in pBiPuro(Sph) to yield pBiEnvDHDR254.

pBiEnvDHDR254 is designed to accept the combinatorial library between a unique Sph I site in the polylinker region and the unique Bam HI site present in the MLV env gene.

The method as detailed above employs a traditional restriction digestion/ligase based method for subcloning the combinatorial library into a screening vector. The method also includes the use of additional subcloning methods, such as TA overhang cloning and T4 DNA pol exo overhang generations for ligase-free subcloning.

H. Linker Sets and Exo-rescue PCR Primers for Arms Generation.

(Note: not all sequence are written 5'→3' so as to emphasize overlaps)

1. Left ann duplex linker (terminates the 3' end of the left arms):

5'-pd(CGGGAGACGGTATGGGCAACT CTCGAG CGG)-3' SEQ ID NO:9

3'-d(GCCCTCTGCCATACCCGTTGA GAGCTC GCC)-5' SEQ ID NO:10

- - - C region - - - M site

2. Exo rescue pair, left arms:
   a. Left interior exo rescue primer 3'-d(GCCCTCTGCCATACCCGTTGA)-Bio-5' SEQ ID NO:11
   b. Left exterior exo-rescue primer (region complementary to the 5' end of the MLV cDNA, lower-case) (unique region introduced by primer, underlined) 5'-pd(ACGGGATCTTGCCTgqtaagctggccatatga)-3' SEQ ID NO:12

3. Right arm duplex linker (initiates the 5' end of the right arms)

5'-d(TCC CCGCGGAAGCCCTCCTCATCATGGGAT TTC)-3' SEQ ID NO:13

3'-d(AGG GGCGCC TTCGGGAGGAGTAGTACCCTA AAG)dp-5' SEQ ID NO:14

- - - M site - - - C region - - -

4. Exo rescue pair, right arms:
   a. Right interior exo rescue primer 5'-Bio-d(AAGCCCTCCTCATCATGGGATTTC)-3' SEQ ID NO:15
   b. Right exterior exo rescue primer (region complementary to the 3' end of the MLV cDNA, underlined) (unique region introduced by primer, underlined) 3'-d(atgcaaac atacagaggc cAGTCCTGGGCCCTA)-5' SEQ ID NO:16

5. SOE pull through primers
   a. left SOE pull through primer (lowercase=overlap with exterior exo primer above) (underlined=sequences not present in starting template) 5' d(GTGATCGCATGCTTCGAacgggatcttgcctggt)-3' SEQ ID NO:17
   b. right SOE pull through primer (lowercase=overlap with exterior exo primer above) (underlined=sequences not present in starting template) 3'-d(gc cagtcctgggccctaACTGGAAACCCTAGGGTACTG)-5' SEQ ID NO:18

6. Marked HDR domain rescue primers
   a. Ligand D 5'-d(CGGGAGACGGTATGGGCAACT)-3' SEQ ID NO:19
   b. Ligand E 3'-d(TTCGGGAGGAGTAGTACCCTA AAG)-5' SEQ ID NO:20

Example II

Screening a Permuted, Chimeric env Gene Library

The following experiment demonstrates a method for screening a library of permuted, chimeric env genes, in which a cDNA encoding a protein or protein domain A is inserted at random between various domains of an ecotropic MLV env gene. These chimeras are intended to permit targeted binding and directed infection by the retrovirus against cells not normally susceptible to infection by the particular strain of retrovirus. The targeted binding is a consequence of the natural ability of the protein domain A to mediate physical interactions between the retroviral virion and the target cell (e.g., domain A is a ligand, while the cells bear a cognate receptor for the ligand, or domain A is an antibody or antibody fragment and the cells bear a surface antigen recognized by the antibody).

The chimeric permuted env gene is prepared as described above in Example I, substituting a wild type, ecotropic env gene for the HDR-deleted env gene used above, and substituting a randomly digested protein A gene for the HDR ligand domain used above.

The screening method relies upon the fact that the genes within a retroviral vector are expressed in both the viral producer cells and within the target cells transduced by the virus. By constructing a bicistronic retroviral vector, a gene which is useful in a genetic screen for successful retroviral-mediated transduction (e.g. an antibiotic resistance marker) will be physically linked to a gene encoding a chimeric retroviral envelope-protein. Expression of the chiimeric env protein from retroviral vector transcripts in the producer cells should permit formation of chimeric virions which contain both chimeric targeting env proteins and wild-type env proteins (which may or may not be required to mediate in retroviral fusion in the presence of chimeric env proteins). If these chimeric virions bear env-fusion proteins which are competent to bind their molecular targets on the surface of the target cells, the target cells will be transduced with the resistance gene. When transduction has occurred, applying selection pressure to the target cells will afford drug resistant colonies bearing the proviral form of the vector, in which the gene for the resistance marker is contiguous with the chimeric gene that permitted successful binding and infection of the target cell. PCR rescue of the chimeric env gene then permits subsequent testing to demonstrate conclusively that the chimera so isolated is capable of mediating targeting of the retrovirus.

A. Reagents Constructed in Order to Apply the Screen

Retroviral protein producer constructs. Retroviral packaging cells are designed to constitutively express retroviral proteins required for virion assembly. Two specific constructs are made that produce spleen necrosis virus (SNV) gag, pol, and env proteins constitutively (FIG. 3). These constructs are pZeoRSVgpING and pHygroCMVenv.

The pZeoRSVgpING construct contains a zeocin resistance marker, and an RSV LTR to drive expression of bicistronic transcripts which express SNV gag-pol polyprotein, as well as human nerve growth factor receptor (hNGFr). Two genes are produced from a single transcript by use of an internal ribosome entry sequence (IRES) element located between the gag-pol ORF and the hNGFr ORF. The bicistronic transcript is terminated with a poly-A signal-sequence derived from bovine growth hormone. The purpose of the IRES-hNGFr cistron is to allow surrogate measurement of gag-pol levels using FACS analysis and an antibody to hNGFr, which is a cell surface marker. If high levels of hNGFr are detected on the producer cell surface, it is then known that the cell is likewise expressing high levels of gag-pol polyprotein, since both products are produced from the same RNA transcript. The pHygroCMVenv expression vector permits expression of wild-type SNV env protein from transcripts generated by the CMV immediate early promoter. It also has a hygromycin resistance marker in the plasmid backbone, permitting selection for hygromycin resistant producer cells during packaging cell line construction.

Packaging Cell Line(s). Human 293 cells that express the EBV EBNA-1 antigen (purchased from InVitrogen) are transfected first with pZeoRSVgpING and selected with zeocin to yield EGiP cells. Subclones of EGIP cells expressing high levels of SNV gag-pol polypeptide are then transfected with pHygroCMVenv and selected with hygromycin, yielding Pacco cells. Pacco cells are then ready to accept any retroviral vector which can be packaged into an SNV virion.

Bicistronic retroviral vectors. Construction of the bicistronic vector requires placement of the selectable marker downstream of the IRES element within either an MLV-based (described above in Example I) or SNV-based (not shown) retroviral vector. The resulting vectors are then ready to receive the env-chimera library cDNAs at unique sites upstream of the IRES element. MLV and SNV vectors have been designed in parallel since SNY virions can package either MLV or SNV retroviral RNAs, and there may be differences in the ability of an SNV versus an MLV LTR to drive gene expression in the producer and/or target cells. Additionally, a class of retroviral vectors can be made in which the expression of the env-IRES-marker RNA transcript is driven by an internal promoter in an inverted orientation relative to the retroviral LTRs. The advantage to the internal promoter construction is that promoters with very high activity in the producer cells (e.g. CMV) may be required to get adequate expression of the chimeric env gene in the producer cell, levels which afford chimeric virion assembly. The inverted transcripts again link marker expression with chimera expression (FIG. 4).

B. Vector Creation and the Screen

The library of env chimeras is directionally subcloned into the bicistronic retroviral vector upstream of the IRES element. The library vector plasmids are propagated, harvested and purified en masse according to standard molecular biology techniques. The vector DNA is then transfected into the Pacco cells (or any other compatible retroviral packaging line) to generate virus containing supernatants which are used to infect target cells. Successful transduction of target cells results in proviral DNA integration into the target cell genome. Expression of the selection marker from the proviral genes alters the phenotype of the target cells, which are selected on the basis of this altered phenotype. As the gene for the molecule responsible for successful infection is physically contiguous with the selection marker in the proviral DNA, traditional molecular biological methods are used to rescue the gene for this library member from the target cell (e.g. subcloning of the selected cells, PCR rescue of the DNA from the host cell genome, etc.).

What is claimed is:

1. A method of making a permuted, chimeric nucleic acid library, the method comprising the steps of:
 (i) permuting a selected nucleic acid derived from a virus family selected from the group consisting of a retrovirus, an adenovirus, and an adeno-associated virus by:
  a. providing backbone nucleic acids comprising selected nucleic acid, wherein the backbone nucleic acids have an exonuclease sensitive site A and wherein the backbone nucleic acids comprise primer sequences C and Y flanking opposite sides of the said selected nucleic acids;
  b. bilaterally digesting the backbone nucleic acids at the exonuclease sensitive site A with an exonuclease, wherein the exonuclease permutes said selected nucleic acids from about every one to about every ten nucloetides, to create permuted nucleic acids;
 (ii) creating 5' permuted nucleic acids by:
  a. ligating to part of the permuted nucleic acids adapters comprising an interior primer sequence B; and
  b. amplifying the permuted nucleic acids using primers complementary to interior primer sequence B and primer sequence C, wherein the amplification reaction incorporates an exterior primer sequence D adjacent to primer sequence C;
 (iii) preparing 3' permuted nucleic acids by:
  a. ligating to part of the permuted nucleic acids adapters comprising an interior primer sequence X; and
  b. amplifying the permuted nucleic acids using primers complementary to interior sequence X and primer sequence Y, wherein the amplification reaction incorporates an exterior primer sequence Z adjacent to primer sequence Y;
 (iv) preparing nucleic acid inserts with 5' adapters having interior primer site B, and 3' adapters having interior site X;
 (v) mixing the 5' permuted nucleic acids, the 3' permuted nucleic acids, and the nucleic acid inserts;
 (vi) amplifying the mixture using primers complementary to exterior primers sites D and Z to create permuted, chimeric nucleic acids; and
 (vii) ligating the permuted, chimeric nucleic acids to a vector, thereby creating a permuted, chimeric nucleic acid library.

2. A method of making a permuted, chimeric nucleic acid library, the method comprising the steps of:
 (i) creating 5' permuted nucleic acids by:
  a. providing backbone nucleic acids comprising a delected nucleic acid derived from a virus family selectes from the group consisting of a retrovirus, an adenovirus, and an adeno-associated virus, wherein the backbone nucleic acids have an exonuclease resistant site R that flanks said selected nucleic acid, wherein the backbone nucleic acids have a primer sequence C;
  b. unilaterally digesting the backbone nucleic acids at the exonuclease sensitive site A with an exonuclease, wherein the exonuclease permutes said selected nucleic acids from about every on to about every ten nucleotides, to create permuted nucleic acids;
  c. ligating to the permuted nucleic acids adapters comprising an interior sequence B; and
  d. amplifying the permuted nucleic acids using primers complementary to interior primer sequence B and primer sequence C, wherein the amplification reaction incorporates an exterior primer sequence D adjacent to primer sequence C;
 (ii) creating 3' permuted nucleic acids by:
  a. providing backbone nucleic acids comprising a selected nucleic acid derived from a virus family selected from the group consisting of a retrovirus, an adenovirus, and an adeno-associated virus, wherein the backbone nucleic acids have an exonuclease resistant site R' that flanks said selected nucleic acid, wherein the backbone nucleic acids have exonuclease sensitive site A, and wherein the backbone nucleic acids have a primer sequence Y;
  b. unilaterally digesting the backbone nucleic acids at the exonuclease sensitive site A with an exonuclease, wherein the exonuclease permutes said selected nucleic acids from about every one to about every ten nucleotides, to create permuted nucleic acids;
  c. ligating to the permuted nucleic acids adapters comprising an interior primer sequence X; and
  d. amplifying the permuted nucleic acids using primers complementary to interior primer sequence X and primer sequence Y, wherein the amplification reaction incorporates an exterior primer sequence Z adjacent to primer sequence Y;
 (iii) preparing nucleic acid inserts with 5' adapters containing primer site B and 3' adapters containing primer site X;
 (iv) mixing the 5' permuted nucleic acids, the 3' permuted nucleic acids, and the nucleic acid inserts;
 (v) amplifying the mixture using primers complementary to exterior primers sites D and Z to create permuted, chimeric nucleic acids; and
 (vi) ligating the permuted, chimeric nucleic acids to a vector, thereby creating a permuted, chimeric nucleic acid library.

3. The method of claim 1, wherein the interior or exterior primers are labeled with a ligand, and steps ii(b) and iii(b) further comprise isolating the permuted nucleic acids by affinity purification.

4. The method of claim 2, wherein the interior or exterior primers are labeled with a ligand, and steps i(d) and ii(d) further comprise isolating the permuted nucleic acids by affinity purification.

5. The method of claim 1 or 2, wherein the retrovirus is derived from a retrovirus subfamily Oncovininae, Lentivirinae, or Spumavirinae.

6. The method of claim 5, wherein the nucleic acid, is an env gene, an integrase gene or a long terminal repeat.

7. The method of claim 6, wherein the env gene is selected from the group consisting of amphotropic MLV env, ecotropic MLV env, HIV-1 env, HIV-2 env, HTLV-1 env, HTLV-2 env, FIV env, SIV env, BIV env, avian spleen necrosis virus env, and HFV env.

8. The method of claim 1 or 2, wherein the nucleic acid insert is selected from the group consisting of growth factors, cytokines, and chemokines.

9. The method of claim 1 or 2, wherein the nucleic acid insert encodes a random peptide.

10. The method of claim 1 or 2, wherein the nucleic acid insert is selected from the group consisting of c-kit, I1-2, I1-3, I1-6, IGF-I, IGF-II, INF-γ, FGF, TGF, TNF-α, TNF-β, NGF, BDNF, CNTF, flt31, and protein A.

* * * * *

UNITED STATES PATENT AND TRADEMARK OFFICE
CERTIFICATE OF CORRECTION

PATENT NO.    : 6,322,969 B1
DATED         : November 27, 2001
INVENTOR(S)   : Stull et al.

It is certified that error appears in the above-identified patent and that said Letters Patent is hereby corrected as shown below:

<u>Column 39,</u>
Line 20, insert -- a -- before "selected nucleic acid";
Line 61, delete "delected" and insert -- selected --.

<u>Column 40,</u>
Line 44, delete "primer";
Line 66, delete "Oncovininae" and insert -- Oncovirinae --.

Signed and Sealed this

Third Day of June, 2003

JAMES E. ROGAN
*Director of the United States Patent and Trademark Office*

SEQUENCE LISTING

```
(1) GENERAL INFORMATION:

(iii) NUMBER OF SEQUENCES: 20

(2) INFORMATION FOR SEQ ID NO: 1:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1..20
          (D) OTHER INFORMATION: /note= "primer T3"

(xi) SEQUENCE DESCRIPTION: SEQ ID NO: 1:

AATTAACCCT CACTAAAGGG                                                  20

(2) INFORMATION FOR SEQ ID NO: 2:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: -
          (B) LOCATION: 1..21
          (D) OTHER INFORMATION: /note= "primer RV-SOE#1"

(xi) SEQUENCE DESCRIPTION: SEQ ID NO: 2:

TGTGATATCT CCATTGGTTA C                                                21
```

(2) INFORMATION FOR SEQ ID NO: 3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..39
        (D) OTHER INFORMATION: /note= "primer RV-SOE#2"

(xi) SEQUENCE DESCRIPTION: SEQ ID NO: 3:

```
GTAACCAATG GAGATATCAC AGTAAACAAC AATCTCACC                    39
```

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "primer BHI"

(xi) SEQUENCE DESCRIPTION: SEQ ID NO: 4:

```
GTGGGATCCC AAATGTAAGC CCTG                                    24
```

(2) INFORMATION FOR SEQ ID NO: 5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..29
        (D) OTHER INFORMATION: /note= "primer HD3mut"

(xi) SEQUENCE DESCRIPTION: SEQ ID NO: 5:

```
GAGTTGTCTG GTCAAGCTTG AGTCTGTTC                               29
```

(2) INFORMATION FOR SEQ ID NO: 6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..26
        (D) OTHER INFORMATION: /note= "primer BstEIImut"

(xi) SEQUENCE DESCRIPTION: SEQ ID NO: 6:

```
CCTGGGAGGT ACCCAATGGA GATCGG                                  26
```

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "primer"

(xi) SEQUENCE DESCRIPTION: SEQ ID NO: 7:

AGATCCCCTT GGTTTACC                                                         18

(2) INFORMATION FOR SEQ ID NO: 8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..36
        (D) OTHER INFORMATION: /note= "primer"

(xi) SEQUENCE DESCRIPTION: SEQ ID NO: 8:

GCGCGGCCGC TCGAGCTATG GCTCGTACTC TATAGG                                     36

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = 5' pyrophosphorylated
            cytosine"

(ix) FEATURE:
        (A) NAME/KEY: misc_feature
        (B) LOCATION: 1..30
        (D) OTHER INFORMATION: /note= "left arm duplex linker
            complementary to SEQ ID NO:10"

(xi) SEQUENCE DESCRIPTION: SEQ ID NO: 9:

NGGGAGACGG TATGGGCAAC TCTCGAGCGG                                             30

(2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA

```
    (ix) FEATURE:
         (A) NAME/KEY: misc_feature
         (B) LOCATION: 1..30
         (D) OTHER INFORMATION: /note= "left arm duplex linker
             complementary to SEQ ID NO:9"

(xi) SEQUENCE DESCRIPTION: SEQ ID NO: 10:

CCGCTCGAGA GTTGCCCATA CCGTCTCCCG                                          30

(2) INFORMATION FOR SEQ ID NO: 11:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 1
         (D) OTHER INFORMATION: /mod_base= OTHER
             /note= "N = biotinylated adenine"

(ix) FEATURE:
         (A) NAME/KEY: -
         (B) LOCATION: 1..21
         (D) OTHER INFORMATION: /note= "left interior exo rescue
             primer"

(xi) SEQUENCE DESCRIPTION: SEQ ID NO: 11:

NGTTGCCCAT ACCGTCTCCC G                                                   21

(2) INFORMATION FOR SEQ ID NO: 12:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 1
         (D) OTHER INFORMATION: /mod_base= OTHER
             /note= "N = 5' pyrophosphorylated
             adenine"

(ix) FEATURE:
         (A) NAME/KEY: -
         (B) LOCATION: 1..32
         (D) OTHER INFORMATION: /note= "left exterior exo rescue
             primer"

(xi) SEQUENCE DESCRIPTION: SEQ ID NO: 12:

NCGGGATCTT GCCTGGTAAG CTGGCCATAT GA                                       32

(2) INFORMATION FOR SEQ ID NO: 13:

(i) SEQUENCE CHARACTERISTICS:
         (A) LENGTH: 33 base pairs
         (B) TYPE: nucleic acid
         (C) STRANDEDNESS: double
         (D) TOPOLOGY: linear (ii) MOLECULE TYPE: DNA (ix) FEATURE:
         (A) NAME/KEY: -
         (B) LOCATION: 1..33
```

(D) OTHER INFORMATION: /note= "right arm duplex linker
            complementary to SEQ ID NO:14"

(xi) SEQUENCE DESCRIPTION: SEQ ID NO: 13:

TCCCCGCGGA AGCCCTCCTC ATCATGGGAT TTC                                33

(2) INFORMATION FOR SEQ ID NO: 14:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = 5' pyrophosphorylated
            guanine"

(ix) FEATURE:
        (A) NAME/KEY: -
        (B) LOCATION: 1..32
        (D) OTHER INFORMATION: /note= "right arm duplex linker
            complementary to SEQ ID NO:13"

(xi) SEQUENCE DESCRIPTION: SEQ ID NO: 14:

NAAATCCCAT GTGAGGAGGG CTTCCGCGGG GA                                 32

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = biotinylated adenine"

(ix) FEATURE:
        (A) NAME/KEY: -
        (B) LOCATION: 1..24
        (D) OTHER INFORMATION: /note= "right interior exo rescue
            primer"

(xi) SEQUENCE DESCRIPTION: SEQ ID NO: 15:

NAGCCCTCCT CATCATGGGA TTTC                                          24

(2) INFORMATION FOR SEQ ID NO: 16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "right exterior exo rescue
            primer"

(xi) SEQUENCE DESCRIPTION: SEQ ID NO: 16:

ATCCCGGGTC CTGACCGGAG ACATACAAAC GTA                                    33

(2) INFORMATION FOR SEQ ID NO: 17:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..34
         (D) OTHER INFORMATION: /note= "left SOE pull through
             primer"

(xi) SEQUENCE DESCRIPTION: SEQ ID NO: 17:

GTGATCGCAT GCTTCGAACG GGATCTTGCC TGGT                                   34

(2) INFORMATION FOR SEQ ID NO: 18:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..38
         (D) OTHER INFORMATION: /note= "right SOE pull through
             primer"

(xi) SEQUENCE DESCRIPTION: SEQ ID NO: 18:

GTCATGGGAT CCCAAAGGTC AATCCCGGGT CCTGACCG                               38

(2) INFORMATION FOR SEQ ID NO: 19:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: -
         (B) LOCATION: 1..21
         (D) OTHER INFORMATION: /note= "marked HDR domain resue
             primer ligand D"

(xi) SEQUENCE DESCRIPTION: SEQ ID NO: 19:

CGGGAGACGG TATGGGCAAC T                                                 21

(2) INFORMATION FOR SEQ ID NO: 20:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (ix) FEATURE:

```
        (A) NAME/KEY: -
        (B) LOCATION: 1..24
        (D) OTHER INFORMATION: /note= "marked HDR domain rescue
            primer ligand E"

(xi) SEQUENCE DESCRIPTION: SEQ ID NO: 20:

GAAATCCCAT GATGAGGAGG GCTT                                            24
```